(12) United States Patent  
Sasaki

(10) Patent No.: US 11,878,957 B2  
(45) Date of Patent: Jan. 23, 2024

(54) PROCESS AND APPARATUS FOR UREA PRODUCTION

(71) Applicant: TOYO ENGINEERING CORPORATION, Tokyo (JP)

(72) Inventor: Keigo Sasaki, Narashino (JP)

(73) Assignee: TOYO ENGINEERING CORPORATION, Tokyo (JP)

( * ) Notice: Subject to any disclaimer, the term of this patent is extended or adjusted under 35 U.S.C. 154(b) by 163 days.

(21) Appl. No.: 17/438,907

(22) PCT Filed: Jun. 20, 2019

(86) PCT No.: PCT/JP2019/024514  
§ 371 (c)(1),  
(2) Date: Sep. 13, 2021

(87) PCT Pub. No.: WO2020/183745  
PCT Pub. Date: Sep. 17, 2020

(65) Prior Publication Data  
US 2022/0144763 A1 May 12, 2022

(30) Foreign Application Priority Data

Mar. 14, 2019 (JP) ................................ 2019-047277

(51) Int. Cl.  
*C07C 273/04* (2006.01)
(52) U.S. Cl.  
CPC .................... *C07C 273/04* (2013.01)
(58) Field of Classification Search  
None  
See application file for complete search history.

(56) References Cited

U.S. PATENT DOCUMENTS

| 4,053,507 A | 10/1977 | Inoue et al. |
| 4,864,059 A | 9/1989 | Fujii |

(Continued)

FOREIGN PATENT DOCUMENTS

| CN | 85107834 A | 6/1986 |
| CN | 101166714 A | 4/2008 |

(Continued)

OTHER PUBLICATIONS

Cambridge English Dictionary definition of the word "simultaneously", downloaded from https://dictionary.cambridge.org/us/dictionary/english/simultaneously on Apr. 17, 2023. (Year: 2023).*

(Continued)

*Primary Examiner* — Amy C Bonaparte  
(74) *Attorney, Agent, or Firm* — Foley & Lardner LLP

(57) ABSTRACT

Provided is a novel process and a novel apparatus for urea production capable of performing heat recovery from a relatively low-temperature fluid. A process for urea production includes a synthesis step, a high-pressure decomposition step and a condensation step and includes a) a step of heat-exchanging steam condensate whose temperature is higher than 90° C. with another fluid to cool this steam condensate to 90° C. or less, b) a step of, by heat-exchanging the steam condensate obtained from the step a with a further fluid having a temperature lower than a temperature of the low-pressure steam, heating the steam condensate obtained from the step a, and c) a step of supplying the steam condensate obtained from the step b to the condensation step as the steam condensate for generating the low-pressure steam. An apparatus for performing the process.

24 Claims, 6 Drawing Sheets

(56) References Cited

U.S. PATENT DOCUMENTS

| | | | |
|---|---|---|---|
| 2009/0036712 A1 | 2/2009 | Kojima | |
| 2009/0062566 A1* | 3/2009 | Kojima | C07C 273/04 |
| | | | 29/402.09 |
| 2015/0119603 A1 | 4/2015 | Van Den Tillaart et al. | |
| 2018/0258034 A1 | 9/2018 | Sato et al. | |

FOREIGN PATENT DOCUMENTS

| | | |
|---|---|---|
| EP | 0 155 735 A1 | 9/1985 |
| EP | 1 728 783 A1 | 12/2006 |
| EP | 1 876 171 A1 | 1/2008 |
| GB | 2557080 A | 6/2018 |
| JP | S60-209555 A | 10/1985 |
| JP | H10-120643 A | 5/1998 |
| JP | 2015-519327 A | 7/2015 |
| RU | 2301798 C2 | 6/2007 |
| WO | WO 03/064379 A1 | 8/2003 |
| WO | WO 2017/043391 A1 | 3/2017 |

OTHER PUBLICATIONS

Examination Report issued in co-pending GCC Application No. GC 2020-39294, dated Jul. 28, 2021.

Examination Report issued in co-pending India Patent Application No. 202147045396, dated Dec. 26, 2022.

Office Action issued in co-pending Chinese Patent Application No. 201980094092.5, dated Oct. 9, 2022.

International Search Report and Written Opinion issued in International Patent Application No. PCT/JP2019/024514, dated Sep. 17, 2019.

Dooyeweerd, et al., "Comparison of the Energy Consumptions of Low-Energy Urea Technologies," *Nitrogen No. 143*, pp. 32-38 (May-Jun. 1983).

Gorlovskiy, et al., "Urea Technology" Tekhnologiya Karbamida, p. 320, Part 2 "Tekhniczeskiye Sredstwa Snizheniya Energozatrat," pp. 247-249 (1981).

Office Action (dated Aug. 30, 2022) and Search Report (completed Aug. 24, 2022) issued in Russian Patent Application No. 2021129720/04.

* cited by examiner

PROCESS AND APPARATUS FOR UREA PRODUCTION

CROSS-REFERENCE TO RELATED APPLICATION(S)

This application is the U.S. National Stage of International Patent Application No. PCT/JP2019/024514, filed Jun. 20, 2019, which claims priority from Japanese Patent Application No. 2019-047277, filed Mar. 14, 2019. The contents of these applications are incorporated herein by reference in their entireties.

TECHNICAL FIELD

The present invention relates to a process and an apparatus for producing urea from ammonia and carbon dioxide.

BACKGROUND ART

A process for urea production typically includes a synthesis step, a high-pressure decomposition step, and a condensation step. The process for urea production further includes a purification step and concentration step. In the synthesis step, urea is generated from ammonia ($NH_3$) and carbon dioxide ($CO_2$). Specifically, as indicated by Formula (1), ammonium carbamate ($NH_2COONH_4$) is generated by the reaction of ammonia ($NH_3$) and carbon dioxide ($CO_2$). Furthermore, as indicated by Formula (2), urea ($NH_2CONH_2$) and water ($H_2O$) are generated by a dehydration reaction of ammonium carbamate.

$$2NH_3 + CO_2 \rightarrow NH_2COONH_4 \quad (1)$$

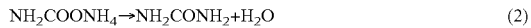
$$NH_2COONH_4 \rightarrow NH_2CONH_2 + H_2O \quad (2)$$

Both reactions are equilibrium reactions and the reaction of Formula (2) is rate-determining as it is slower than the reaction of Formula (1).

In the high-pressure decomposition step, a urea synthesis solution obtained in the synthesis step is heated to decompose the ammonium carbamate contained in the urea synthesis solution into ammonia and carbon dioxide so as to obtain a gaseous mixture containing ammonia and carbon dioxide and a urea synthesis solution having a higher urea concentration. In the condensation step, the gaseous mixture obtained in the high-pressure decomposition step is condensed.

In the purification step, the urea synthesis solution after being processed in the high-pressure decomposition step is heated at a pressure lower than the pressure in the high-pressure decomposition step and higher than the atmospheric pressure to generate a gas phase and a liquid phase. A urea synthesis solution having an increased urea concentration is obtained by separating this gas phase.

In the concentration step, the urea synthesis solution after being processed in the purification step is heated at a pressure lower than the pressure in the purification step and equal to or lower than the atmospheric pressure to generate a gas phase and a liquid phase. A urea synthesis solution with further increased urea concentration is obtained by separating this gas phase.

WO 2017/043391 describes a method in which steam condensate, which is generated in the purification step and/or the concentration step, is used as a heat source for heating raw material ammonia to be supplied to the synthesis step.

In E. Dooyeweerd, et al., "Comparison of the energy consumptions of low-energy urea technologies", Nitrogen No. 143, May-June 1983, pp 32 to 38, steam condensate, which is generated when low-pressure steam is used as a heat source in the purification step and the concentration step, is reduced in pressure to a substantially atmospheric pressure (1.2 bar) and thereafter flushed. Steam having the substantially atmospheric pressure generated thereby is used for heating ammonia.

CITATION LIST

Patent Literature

[PTL 1]
WO 2017/043391

Non-Patent Literature

[NPL 1]
E. Dooyeweerd, et al., "Comparison of the energy consumptions of low-energy urea technologies", Nitrogen No. 143, May-June 1983, pp 32 to 38

SUMMARY OF INVENTION

Technical Problem

The literatures described above teach that a fluid from which heat is to be recovered is heat-exchanged with the raw material ammonia, whereby heat is recovered from the fluid.

However, there is limitations in a flow rate and a temperature of the raw material ammonia. Therefore, when only the above technique, i.e. the heat-exchanging between the fluid from which heat is to be recovered and the raw material ammonia, is used for recovering heat, the degree of flexibility of designing an apparatus for urea production is low. Recovering heat from a relatively low-temperature fluid may be practically difficult or may require a complicated apparatus.

An object of the present invention is to provide a novel process for urea production and a novel apparatus for urea production capable of performing heat recovery from a relatively low-temperature fluid.

Solution to Problem

According to an aspect of the present invention, there is provided a process for urea production, including:
 a synthesis step of synthesizing urea from ammonia and carbon dioxide to generate a urea synthesis solution;
 a high-pressure decomposition step of, by heating the urea synthesis solution generated in the synthesis step, decomposing ammonium carbamate and separating a gaseous mixture containing ammonia and carbon dioxide from the urea synthesis solution; and
 a condensation step of absorbing and condensing at least a part of the gaseous mixture obtained in the high-pressure decomposition step in an absorption medium and generating low-pressure steam from steam condensate with use of heat generated during the condensation, the process for urea production further including:
a) a step of heat-exchanging steam condensate whose temperature is higher than 90° C. with another fluid to cool this steam condensate to 90° C. or less;
b) a step of, by heat-exchanging the steam condensate obtained from the step a with a further fluid having a temperature lower than a temperature of the low-pressure steam, heating the steam condensate obtained from the step a; and c) a step of supplying the steam condensate obtained from the step b to the condensation step as the steam condensate for generating the low-pressure steam.

According to another aspect of the present invention, there is provided an apparatus for urea production, including:

a synthesis reactor configured to synthesize urea from ammonia and carbon dioxide to generate a urea synthesis solution;

a high-pressure decomposer configured to, by heating the urea synthesis solution generated by the synthesis reactor, decompose ammonium carbamate and separate a gaseous mixture containing ammonia and carbon dioxide from the urea synthesis solution; and a condenser configured to absorb and condense at least a part of the gaseous mixture obtained by the high-pressure decomposer in an absorption medium and generate low-pressure steam from steam condensate with use of heat generated during the condensation, the apparatus for urea production further including:

a first heat exchange structure configured to heat-exchange steam condensate whose temperature is higher than 90° C. with another fluid to cool this steam condensate to 90° C. or less;

a second heat exchange structure configured to, by heat-exchanging the steam condensate obtained from the first heat exchange structure with a further fluid having a temperature lower than a temperature of the low-pressure steam, heat the steam condensate obtained from the first heat exchange structure; and a line for supplying the steam condensate obtained from the second heat exchange structure to the condenser as the steam condensate for generating the low-pressure steam.

Advantageous Effects of Invention

According to the present invention, there is provided a novel process for urea production and a novel apparatus for urea production capable of performing heat recovery from a relatively low-temperature fluid.

DESCRIPTION OF EMBODIMENTS

Figure 1:
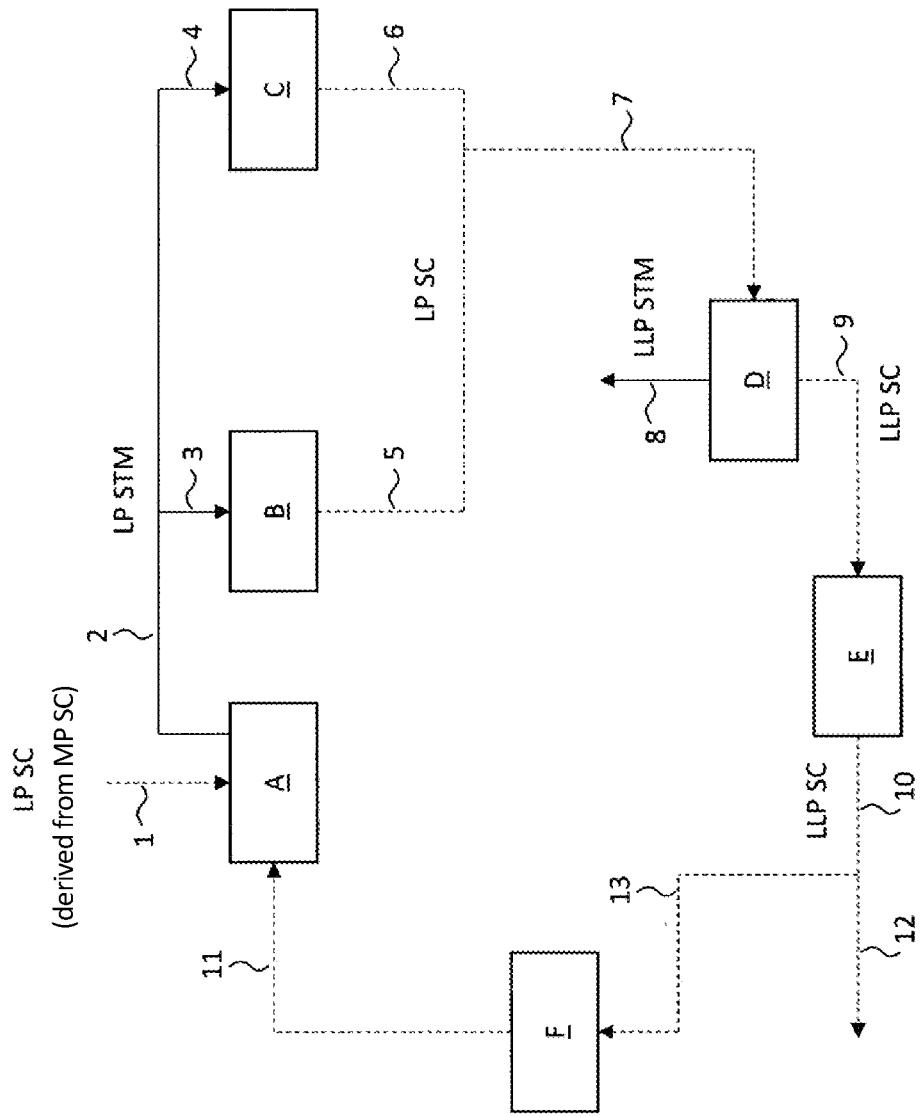
FIG. 1 is a schematic diagram for explaining a process example of a steam/steam condensate system according to the present invention.

A process for urea production according to the present invention includes a synthesis step, a high-pressure decomposition step, and a condensation step. The process for urea production according to the present invention may further include one or more of a purification step, a concentration step, a low-low-pressure fluid generation step, a recovering step, a medium-low-pressure steam generation step and a granulation step. Ammonia and carbon dioxide as raw materials can be supplied to one or more of the synthesis step, the high-pressure decomposition step, the condensation step, the purification step, and the recovering step from the outside.

An apparatus for urea production for performing such a process for urea production includes a synthesis reactor, a high-pressure decomposer and a condenser for respectively performing the synthesis step, the high-pressure decomposition step and the condensation step. The apparatus for urea production may further include one or more of a purification apparatus, a concentration apparatus, a low-low-pressure fluid generating apparatus, a recovering apparatus, a medium-low-pressure steam generating apparatus and a granulating apparatus for respectively performing the purification step, the concentration step, the low-low-pressure fluid generation step, the recovering step, the medium-low-pressure steam generation step and the granulation step.

Steam condensate means water obtained by condensing steam in the apparatus for urea production. However, make-up water may be added to the steam condensate from the outside. When hot water is used as a cooling medium in heat exchange, the hot water is water having a temperature higher than the temperature of utility cooling water when the hot water is supplied to the heat exchange and remains as liquid even after the heat exchange (that is, does not boil). The hot water may be pressurized for preventing boiling as necessary. The temperature of the hot water will be explained below concerning the recovering step.

[Synthesis Step]

In the synthesis step, urea is synthesized from ammonia and carbon dioxide to generate a urea synthesis solution. In the synthesis step, urea is also synthesized from ammonium carbamate contained in a recycled liquid from the condensation step that will be described later.

The operating pressure in the synthesis step is typically 130 bar (absolute pressure, which also applies to the following description) to 250 bar, preferably 140 bar to 200 bar. The operating temperature in the synthesis step is typically 160° C. to 200° C., preferably 170° C. to 190° C.

[High-Pressure Decomposition Step]

In the high-pressure decomposition step, the urea synthesis solution generated in the synthesis step is heated, typically with use of medium-pressure steam as a heat source. By heating the urea synthesis solution, ammonium carbamate contained in the urea synthesis solution obtained in the synthesis step is decomposed and a gaseous mixture containing ammonia and carbon dioxide is separated from the urea synthesis solution. The gaseous mixture obtained in the high-pressure decomposition step may be hereinafter referred to as "high-pressure decomposition outlet gas". By condensation of the medium-pressure steam used as the heat source, medium-pressure steam condensate is generated.

Heating in the high-pressure decomposition step requires a high-temperature heating medium. Typically, low-pressure steam generated in the condensation step, which will be described later, does not have a sufficiently high temperature for the heating. Therefore, medium-pressure steam having a pressure higher than the pressure of the low-pressure steam is used in the heating.

The pressure of the medium-pressure steam is typically 12 bar to 40 bar, preferably 14 bar to 25 bar. The medium-pressure steam is often appropriately generated as back-pressure steam of a steam turbine in an apparatus for urea production. Superheated steam obtained as the back-pressure steam is often appropriately brought into contact with steam condensate to be converted to saturated steam, and then used for the heating. Therefore, typically, the temperature of the medium-pressure steam is a saturation temperature of water at the pressure of the medium-pressure steam. The pressure and the temperature of the medium-pressure steam condensate are about the same as the pressure and the temperature of the medium-pressure steam. Alternatively, the medium-pressure steam can be supplied from the outside of the apparatus for urea production.

The operating temperature in the high-pressure decomposition step is typically 150° C. to 220° C., preferably 160° C. to 200° C.

Specifically, the urea synthesis solution obtained in the synthesis step contains urea, ammonia, carbon dioxide, ammonium carbamate, and water. The urea synthesis solution is typically heated under a pressure substantially equal to the pressure in the synthesis step. Consequently, the ammonia, carbon dioxide, ammonium carbamate, and water are separated as a gaseous mixture containing ammonia, carbon dioxide, and water (steam).

In the high-pressure decomposition step, it is possible to use a decomposition method in which only heating is performed. However, in order to promote decomposition, it is possible to use a stripping process in which, in addition to heating, carbon dioxide gas is brought into contact with a urea synthesis solution.

[Condensation Step]

In the condensation step, at least a part of the gaseous mixture (high-pressure decomposition outlet gas) obtained in the high-pressure decomposition step is absorbed and condensed in an absorption medium. Low-pressure steam is generated from steam condensate with use of heat generated during the condensation. When the low-pressure steam is used as a heat source for heating another fluid, low-pressure steam condensate is generated by condensation of the low-pressure steam.

The low-pressure steam should have a pressure under which the saturation temperature of water is lower than the temperature of the process fluid in the condensation step. On the other hand, in consideration of utilizing the generated low-pressure steam in another step of the process for urea production, the pressure of the low-pressure steam is preferably high to some extent. From such viewpoints, the pressure of the low-pressure steam is typically 3 bar to 9 bar, preferably 4 bar to 7 bar. Typically, the temperature of the low-pressure steam is a saturation temperature of water at the pressure of the low-pressure steam. The pressure and the temperature of the low-pressure steam condensate are about the same as the pressure and the temperature of the low-pressure steam.

As the absorption medium used in the condensation step, an absorption medium publicly known in the field of the process for urea production, such as water (which may contain urea, ammonia, carbon dioxide and ammonium carbamate), may be appropriately used.

The temperature of liquid (process fluid) obtained in the condensation step is typically 100° C. to 210° C., preferably 160° C. to 190° C., in particular, when a balance of reaction and condensation is considered. Since the high-pressure process (including the synthesis step, the high-pressure decomposition step and the condensation step) in urea production has nothing that results in pressure reduction except pressure loss, the synthesis step, the high-pressure decomposition step and the condensation step are operated at substantially the same pressure. It should be noted that pressurization by an ejector is performed for recycling which will be described later.

Specifically, the gaseous mixture (the high-pressure decomposition outlet gas) separated in the high-pressure decomposition step is introduced into the condensation step, where the gaseous mixture comes into contact with the absorption medium containing water under cooling, and where the gaseous mixture condenses. During the condensation, a part of ammonia and a part of carbon dioxide turn into ammonium carbamate (see Formula (1)), and, the urea synthesis reaction (see Formula (2)) also progresses by keeping the condensation temperature high.

When the gaseous mixture condenses in the condensation step, a large amount of heat is generated. Heat recovery is performed in order to effectively use the heat. As a method for the heat recovery, there is a method in which heat is exchanged between the urea synthesis solution after being processed in the high-pressure decomposition step and an internal fluid (process fluid) of the condenser. Alternatively, there is a method of performing heat exchange between the internal fluid (process fluid) of the condenser and hot water (pressurized water is often used) to obtain hot water having a higher temperature. In many cases, however, a method of performing heat exchange between the internal fluid (process fluid) of the condenser and steam condensate (in particular, low-pressure steam condensate) to generate low-pressure steam is used. This method may be used in combination with at least one of the two methods described above.

As described above, in the condensation step, the supply of the steam condensate is necessary in order to generate the low-pressure steam through the heat recovery. For example, when a vessel for storing low-pressure steam condensate is used separately from the condenser in the condensation step, the low-steam condensate can be supplied to the vessel and transferred from the vessel to the condenser. In the present specification, steam condensate supplied to the condensation step (the condenser) in order to generate the low-pressure steam may be referred to as "condensation-step-supply steam condensate".

The medium-pressure steam condensate generated in the high-pressure decomposition step is often reduced in pressure and used as the condensation-step-supply steam condensate. In this case, the medium-pressure steam condensate is sometimes used as the condensation-step-supply steam condensate after the medium-pressure steam condensate is used as a heat source in another step and its temperature is lowered. In any case, since the amount of the low-pressure steam generated in the condensation step is large, the amount of the medium-pressure steam condensate generated in the high-pressure decomposition step is generally insufficient for a necessary amount of the condensation-step-supply steam condensate. Therefore, steam condensate generated after the low-pressure steam is used as a heat source in the apparatus for urea production may be pressurized by a pump and used as the condensation-step-supply steam condensate for generating low-pressure steam in the condensation step.

For the heat exchange between the internal fluid (process fluid) of the condenser and the steam condensate, a vertical or horizontal shell & tube heat exchanger may be used. The gaseous mixture may be condensed on the tube side, or the gaseous mixture may be condensed on the shell side so that residence time in the condensation step can be long for the sake of condensation and reaction.

Gas remaining uncondensed in the condensation step (process-side of the condenser) can, after being appropriately reduced in pressure, be absorbed and condensed in an absorption medium (liquid), and the absorption medium, which has absorbed the gas, can be simultaneously cooled. Consequently, recovered liquid containing ammonia and carbon dioxide can be obtained (recovering step).

[Recycling]

The condensed liquid (the absorption medium which has absorbed at least a part of the high-pressure decomposition outlet gas) obtained in the condensation step may be sent to the synthesis step again. Accordingly, it is possible to adopt a method of recycling, among the synthesis step, the high-pressure decomposition step and the condensation step, the unreacted ammonia and the unreacted carbon dioxide which have not converted into urea. As a method for recycling the condensed liquid obtained in the condensation step, there is a method in which a synthesis reactor (for performing the synthesis step) is arranged below, and a condenser (for performing the condensation step) is arranged above the synthesis reactor so as to recycle the condensed liquid using gravity. As another recycling method, there is a method in which, with use of raw material ammonia to be supplied to a synthesis reactor as a driving fluid of an ejector, a condensed liquid obtained in the condensation step is pressurized by the ejector to recycle the condensed liquid. The recycling method using gravity and the recycling method using an ejector may be used in combination.

[Purification Step and Condensation Step]

The urea synthesis solution after being processed in the high-pressure decomposition step is subjected to processing by pressure reduction and heating. By this processing, ammonia, carbon dioxide and ammonium carbamate, which have not been separated, and water are separated as a gaseous mixture (a gas phase) containing ammonia, carbon dioxide and water (steam). Consequently, a urea synthesis solution (a liquid phase) having an increased urea concentration can be obtained.

The gaseous mixture can be recovered to obtain a recovered liquid, when the gaseous mixture is absorbed and condensed in an absorption medium (liquid) and the absorption medium, which has absorbed the gas, is simultaneously cooled (a recovering step).

In such processing by the pressure reduction and the heating, it is easier to separate ammonia, carbon dioxide and ammonium carbamate, which have not been separated, and water as a gaseous mixture by the heating, when the urea synthesis solution after being processed in the high-pressure decomposition step is reduced in pressure as much as possible. On the other hand, in order to cause the separated gaseous mixture to be absorbed into an absorption medium and in order to return the obtained recovered liquid to the high-pressure process, it is advantageous that the pressure of the urea synthesis solution is as high as possible in the processing by the pressure reduction and the heating. Therefore, it is possible to divide the processing by the pressure reduction and the heating into a plurality of stages in which pressures are different from one another, and to subject the urea synthesis solution after being processed in the high-pressure decomposition step to said plurality of stages. Consequently, it is possible to efficiently separate and recover ammonia, carbon dioxide, ammonium carbamate and water to obtain a high-purity urea synthesis solution. To this end, the purification step and the concentration step are performed.

In both of the purification step and the concentration step, the low-pressure steam generated in the condensation step may be used as a heat source. The low-pressure steam has a lower temperature compared with that of the medium-pressure steam which is used as the heat source in the high-pressure decomposition step.

In both of the purification step and the concentration step, medium-steam condensate may be used, and/or steam which is generated by reducing in pressure the medium-pressure steam condensate may be used, as the heat source in addition to the low-pressure steam. The medium-pressure steam condensate is steam condensate generated when the medium-pressure steam is used as a heat source. It is possible to obtain steam and steam condensate which have a lower pressure than the pressure of the medium-pressure steam by reducing in pressure the medium-pressure steam condensate.

[Purification Step]

In the purification step, a gas phase and a liquid phase are generated by heating the urea synthesis solution after being processed in the high-pressure decomposition step at a pressure lower than the pressure in the high-pressure decomposition step and higher than the atmospheric pressure with use of, as the heat source, a part of the low-pressure steam generated in the condensation step. At this time, ammonium carbamate contained in the urea synthesis solution after being processed in the high-pressure decomposition step can be decomposed. A urea synthesis solution having an increased urea concentration is obtained by separating the gas phase from the liquid phase. Low-pressure steam condensate is generated from the low-pressure steam which has been used as the heat source.

Therefore, in the purification step, pressure reduction operation is performed at least once and heating operation is performed at least once. The purification step may be performed in one stage or may be performed in a plurality of stages. For example, the purification step may be performed in two stages consisting of a medium-pressure decomposition step and a low-pressure decomposition step.

The medium-pressure decomposition step is a step of reducing in pressure the urea synthesis solution directly after being processed in the high-pressure decomposition step to a pressure higher than the atmospheric pressure, heating the urea synthesis solution as necessary, generating a gas phase (a gaseous mixture) and a liquid phase, and separating the gas phase. However, as explained above, heat recovery is sometimes performed in the condensation step by heat exchange between the urea synthesis solution directly after being processed in the high-pressure decomposition step and the internal fluid (process fluid) of the condenser. In this case, the medium-pressure decomposition step means a step of heating, at a pressure lower than the pressure in the high-pressure decomposition step, the urea synthesis solution after being heated by this heat recovery to separate a gaseous mixture.

In the medium-pressure decomposition step, the low-pressure steam can be used as the heat source. In the medium-pressure decomposition step, ammonium carbamate contained in the urea synthesis solution after being processed in the high-pressure decomposition step is decomposed. A gaseous mixture containing ammonia and carbon dioxide (this gaseous mixture may be hereinafter referred to as "medium-pressure decomposition outlet gas") and a urea synthesis solution having a decreased ammonium carbamate concentration are obtained from the medium-pressure decomposition step.

The operating pressure in the medium-pressure decomposition step depends on the number of the stages of the processing by the pressure reduction and the heating. For example, in the case of two stages (the medium-pressure decomposition step and the low-pressure decomposition step), the operating pressure is typically 3 bar to 130 bar, preferably 6 bar to 70 bar, and more preferably 10 bar to 20 bar. The operating temperature of the medium-pressure decomposition step depends on the operating pressure but is typically 100° C. to 180° C., preferably on the order of 130° C. to 170° C.

In the low-pressure decomposition step, after the medium pressure decomposition step, the urea synthesis solution after being processed in the medium-pressure decomposition step may be reduced in pressure and/or heated at a pressure lower than the pressure in the medium-pressure decomposition step (and equal to or higher than the atmospheric pressure). A gaseous mixture containing ammonia and carbon dioxide (this gaseous mixture may be hereinafter referred to as "low-pressure decomposition outlet gas") and a urea synthesis solution having a further reduced ammonium carbamate concentration are obtained from the low-pressure decomposition step.

The operating pressure in the low-pressure decomposition step is typically 1.5 bar to 6 bar, preferably 2 bar to 4 bar. The operating temperature in the low-pressure decomposition step depends on the operating pressure but is typically 90° C. to 170° C., preferably on the order of 110° C. to 150° C.

A purification apparatus that performs the purification step may include a pressure reducing valve for performing the pressure reduction, a heat exchange structure for performing the heating, and a gas-liquid separation structure. For example, a medium-pressure decomposer for performing the medium-pressure decomposition step may include a structure for heat exchange between steam which functions as a heat source and a process fluid (urea synthesis solution). A pressure reducing valve for performing the pressure reduction may be disposed upstream of the medium-pressure decomposer in relation to the flow direction of the process fluid (urea synthesis solution).

[Concentration Step]

In the concentration step, a gas phase and a liquid phase are generated by heating the urea synthesis solution after being processed in the purification step at a pressure lower than the pressure in the purification step (pressure after the last pressure reduction operation in the purification step) and equal to or lower than the atmospheric pressure with use of, as the heat source, another part of the low-pressure steam generated in the condensation step. A urea synthesis solution having a further increased urea concentration is obtained by separating the gas phase from the liquid phase. Low-pressure steam condensate is generated from the low-pressure steam which has been used as the heat source. In the concentration step, the content of water contained in the urea synthesis solution is reduced by performing heating under the atmospheric pressure or under vacuum.

Therefore, in the concentration step, pressure reduction operation is performed at least once and heating operation is performed at least once. The concentration step may be performed in one stage or may be performed in a plurality of stages. For example, the concentration step may be performed in two stages.

Conditions for the concentration step depend on a granulation method. For example, the concentration in two stages may be performed under conditions described below to manufacture solid urea in the form of prill:

First Stage
urea concentration: 80 to 98 mass %,
pressure: 100 mmHg (0.13 bar) to 500 mmHg (0.67 bar), preferably 150 mmHg (0.20 bar) to 350 mmHg (0.47 bar),
temperature: 125 to 140° C.

Second Stage
urea concentration: 94 to 99.9 mass %,
pressure: 10 mmHg (0.013 bar) to 100 mmHg (0.13 bar), preferably 15 mmHg (0.020 bar) to 50 mmHg (0.067 bar),
temperature: 130 to 145° C.

A concentration apparatus that performs the concentration step may include a pressure reducing valve for performing the pressure reduction, a heat exchange structure for performing the heating, and a gas-liquid separating structure. Urea synthesis solution obtained from the concentration step may be obtained as product urea, or a granulation step may be performed following the concentration step to obtain granular product urea.

[Low-Low-Pressure Fluid Generation Step]

In the low-low-pressure fluid generation step, low-low-pressure steam condensate and low-low-pressure steam are generated by reducing in pressure at least a part of the low-pressure steam condensate obtained from one or both of the purification step and the concentration step to a pressure equal to or higher than the atmospheric pressure. The low-low-pressure steam condensate and low-low-pressure steam has a pressure equal to or higher than the atmospheric pressure and lower than the pressure of the low-pressure steam condensate obtained from one or both of the purification step and the concentration step. Therefore, the low-low-pressure steam condensate and the low-low-pressure steam have a pressure lower than the pressure of the low-pressure steam generated in the condensation step. The low-low-pressure steam condensate and the low-low-pressure steam having a pressure higher than the atmospheric pressure respectively have higher usefulness compared with steam condensate and steam having the atmospheric pressure.

A low-low-pressure fluid generating apparatus used for performing the low-low-pressure fluid generation step may include a pressure reducing valve and may further include a gas-liquid separator (vessel).

From the viewpoint of setting the temperature of the low-low-pressure steam and the low-low-pressure steam condensate relatively high, the pressure of the low-low-pressure steam and the low-low-pressure steam condensate is preferably 2 bar or more, more preferably 3 bar or more. A pressure difference between the pressure of the low-low-pressure steam and the low-low-pressure steam condensate and the pressure of the low-pressure steam generated in the condensation step is preferably 1 bar or more, more preferably 2 bar or more. When the pressure difference is within the abovementioned range, it is easy to cause the low-pressure steam condensate to flow into the low-low-pressure fluid generating apparatus and generate low-low-pressure fluid. Typically, the temperature of the low-low-pressure steam and the low-low-pressure steam condensate in the low-low-pressure fluid generation step is a saturation temperature of water at the pressure of the low-low-pressure steam and the low-low-pressure steam condensate. The temperature of the low-low-pressure steam and the low-low-pressure steam condensate can be changed by heat exchange that is performed after the low-low-pressure fluid generation step.

[Recovering Step]

In the recovering step, at least one of gas I and gas II described below is absorbed and condensed in an absorption medium (liquid) and the absorption medium, which has absorbed the at least one gas, is simultaneously cooled. Consequently, recovered liquid containing ammonia and carbon dioxide is obtained.

Gas I) Gas remaining uncondensed in the condensation step.
Gas II) Gas obtained as the gas phase separated in the purification step when the process for urea production includes the purification step.

The gas I may be appropriately reduced in pressure before the absorption and the condensation. When the purification step is performed in two stages (a medium-pressure decomposition step and a low-pressure decomposition step), in particular, a gas phase separated in the medium-pressure decomposition step may be used as the gas II.

By returning the recovered liquid, after being appropriately pressurized, to the high-pressure process (including the synthesis step, the high-pressure decomposition step and the condensation step), typically to the condensation step, unreacted ammonia and unreacted carbon dioxide can be recovered. As the absorption medium, an absorption medium publicly known in the field of the process for urea production, such as water (which may contain urea, ammonia, carbon dioxide, and ammonium carbamate) can be appropriately used.

When a plurality of gasses is used as the gas I and/or the gas II, two or more gases among these gases may be appropriately mixed and supplied to the recovering step.

Further, at least a part of the gas I and/or the gas II may be brought into gas-liquid contact with an absorption medium upstream of the recovering step, and heat generated during condensation at this time may be used for heating the urea synthesis solution in the concentration step. In this case, generally, a heat exchanger is used for the heat exchange. The absorption medium used in this case may be the same as the absorption medium used in the recovering step.

Hot water may be used as a cooling medium for the cooling (cooling of liquid that has absorbed at least one of the gas I and the gas II) in the recovering step. The temperature of the cooling medium (the hot water) supplied to the recovering step is, for example, about 50 to 110° C., typically, about 90 to 100° C. The hot water of, for example, about 70 to 120° C., typically, about 90 to 110° C. is discharged from the recovering step. The pressure of the cooling medium (the hot water) used in the recovering step is, for example, about 2 to 6 bar.

A supply temperature of the absorption medium to the recovering step is, for example, about 40 to 100° C. A discharge temperature of the absorption medium from the recovering step is, for example, about 90 to 120° C. The pressure of the absorption medium used in the recovering step may be about the same as the pressure of the gas cooled in the recovering step.

[Medium-Low-Pressure Steam Generation Step]

When medium-pressure steam condensate is obtained from the high-pressure decomposition step, the medium-pressure steam condensate may be reduced in pressure to a medium-low pressure to generate medium-low-pressure steam and medium-low-pressure steam condensate (the medium-low-pressure steam generation step). A medium-low-pressure steam generating apparatus used for this purpose may include an appropriate pressure reducing valve for pressure reduction and may include a gas-liquid separator for separating the generated medium-low-pressure steam and medium-low-pressure steam condensate.

The medium-low pressure means a pressure lower than the pressure of the medium-pressure steam and higher than the pressure of the low-pressure steam. The pressure of the medium-low-pressure steam and the medium-low-pressure steam condensate is, for example, 7 bar to 18 bar, preferably, 8 bar to 12 bar. Typically, the temperature of the medium-low-pressure steam and the medium-low-pressure steam condensate is a saturation temperature of water at the pressure of the medium-low-pressure steam and the medium-low-pressure steam condensate.

By pressurizing the low-pressure steam with an ejector using the medium-pressure steam as a driving fluid, medium-low-pressure steam having a pressure lower than the pressure of the medium-pressure steam and higher than the pressure of the low-pressure steam may be generated. The medium-low-pressure steam may be generated by pressurizing the low-pressure steam with an ejector using high-pressure steam, which has a higher pressure than the medium-pressure steam, as a driving fluid. The ejector using the medium-pressure steam as the driving fluid and the ejector using the high-pressure steam as the driving fluid may be used together. The high-pressure steam is, for example, steam supplied to a steam turbine. By this step, it is possible to increase heat sources having a temperature higher than the temperature of the low-pressure steam while effectively utilizing the low-pressure steam.

[Granulation Step]

The method for urea production may include a granulation step of producing granular solid urea, with use of air, from the urea synthesis solution which has been processed in the concentration step. The granulation step may include a step of heating the air. The heating of the air is performed to, for example, raise the temperature of the air from the outside and reduce the relative humidity of the air. In order to perform the granulation step, it is possible to use an apparatus in which an appropriate heat exchange structure is provided in a granulator which is publicly known in the field of urea production.

[Heat Recovery from a Fluid Having a Relatively Low Temperature (Steps a to c)]

The process for urea production of the present invention includes steps a to c.

a) step of heat-exchanging steam condensate whose temperature is higher than 90° C. with another fluid to cool the steam condensate to 90° C. or less, b) a step of heating the steam condensate obtained from the step a by heat-exchanging the steam condensate obtained from the step a with a further fluid (this may be hereinafter referred to as "heat recovery target fluid") having a temperature lower than the temperature of the low-pressure steam (the low-pressure steam generated in the condensation step), and c) a step of supplying the steam condensate obtained from the step b to the condensation step as the steam condensate for generating the low-pressure steam.

In the step a, the temperature of the steam condensate whose temperature is higher than 90° C. is lowered. In the step b, heat is recovered from the heat recovery target fluid by using the steam condensate after the lowering of the temperature. The steam condensate after being used for the heat recovery, that is, the steam condensate heated in the step b is supplied to the condensation step. With these steps, the heat recovery can be easily performed from a fluid having a relatively low temperature. This is effective for reducing an amount of steam used as a heat source in the apparatus for urea production.

A part of the steam condensate lowered in temperature in the step a may be discharged to the outside of the apparatus for urea production (to, for example, a boiler water supply adjusting apparatus) and the remaining part may be supplied to the step b. In this case, since the temperature of the steam condensate discharged to the outside is low, heat which is taken out from the apparatus for urea production by the steam condensate discharged to the outside is less. In addition, for example, if the temperature of the steam condensate supplied to the boiler water supply adjusting apparatus is low, this is sometimes advantageous from the viewpoint of a heat-resistant temperature of the boiler water supply adjusting apparatus.

In order to perform the steps a to c, a heat exchange structure, a pressurizing device, piping, and the like may be used in combination as appropriate.

[Step a]

In the step a, the steam condensate whose temperature is higher than 90° C. is heat-exchanged with another fluid and cooled to 90° C. or less.

As the steam condensate supplied to the step a, it is possible to use, as appropriate, steam condensate whose temperature is higher than 90° C. among steam condensates which are present in the apparatus for urea production. The temperature of the steam condensate supplied to the step a is, for example, about 100 to 220° C., typically, about 100 to 170° C. The temperature of the steam condensate discharged from the step a is 90° C. or less, for example, about 30 to 70° C., typically, about 50° C. The pressure of the steam condensate used in the step a is, for example, the atmospheric pressure to about 25 bar.

As the "another fluid" used in the step a, it is possible to use, as appropriate, a fluid having a temperature equal to or lower than 90° C., for example, a temperature of about 30 to 50° C. among fluids which are present in the apparatus for urea production. The temperature of the "another fluid" discharged from the step a is lower than the temperature of the steam condensate whose temperature is higher than 90° C. supplied to the step a.

In order to perform the step a, an appropriate heat exchange structure (this may be hereinafter referred to as "first heat exchange structure") may be used. In the first heat exchange structure, the steam condensate whose temperature is higher than 90° C. is supplied to a high-temperature side and the "another fluid" is supplied to a low-temperature side.

[Step b]

In the step b, the steam condensate obtained from the step a is heated by heat-exchanging the steam condensate obtained from the step a with the heat recovery target fluid. In other words, heat is recovered from the heat recovery target fluid. The steam condensate obtained in the step a may be supplied to the step b. The step b may be performed in only one stage, or may be performed in a plurality of stages. For example, when the step b is performed in two stages, the steam condensate obtained in the step a may be supplied to the first stage of the step b and heated. Then the steam condensate obtained from the first stage of the step b may be supplied to the second stage of the step b and further heated.

The temperature of the steam condensate supplied to the step b is, for example, about 30 to 70° C. The temperature of the steam condensate discharged from the step b is lower than the temperature of the low-pressure steam.

As the heat recovery target fluid, it is possible to use, as appropriate, a fluid having a temperature lower than the temperature of the low-pressure steam among the fluids which are present in the apparatus for urea production.

In order to perform the step b, an appropriate heat exchange structure (this may be hereinafter referred to as "second heat exchange structure") may be used. In the second heat exchange structure, the steam condensate obtained from the step a is supplied to a low-temperature side and the further fluid (the heat recovery target fluid) is supplied to a high-temperature side.

[Step c]

In step c, the steam condensate obtained from the step b is supplied to the condensation step as the condensation-step-supply steam condensate. In order to perform the step c, a line for supplying steam condensate, which is obtained from the second heat exchange structure, to the condenser as the condensation-step-supply steam condensate may be used. That is, a line connecting a low-temperature side outlet of the second heat exchange structure and an inlet of the condensation-step-supply steam condensate (a cooling side inlet) of the condenser may be used.

Embodiments of the steam condensate supplied to the step a, the "another fluid" supplied to the step a, and the heat recovery target fluid from which heat is recovered in the step b are explained below. The embodiments explained below may be used in combination as appropriate.

Embodiment 1.1: A First Embodiment of the Steam Condensate Supplied to the Step a In this embodiment, the process for urea production includes the purification step, the concentration step and the low-low-pressure fluid generation step. As the steam condensate (exceeding 90° C.) supplied to the step a, low-low-pressure steam condensate generated in the low-low-pressure fluid generation step is entirely or partially used. In this embodiment, the pressure of the steam condensate supplied to the step a is relatively low. Therefore, a design pressure of apparatus for performing the steps a and b can be set lower.

The temperature of the low-low-pressure steam condensate supplied to the step a is typically the boiling point of water at the abovementioned pressure of the low-low-pressure steam condensate (a pressure equal to or higher than the atmospheric pressure). For example, by reducing the pressure of at least a part of the low-pressure steam condensate obtained from one or both of the purification step and the concentration step to a pressure of the atmospheric pressure or more, preferably, to 2 bar or more, steam condensate having a pressure of the atmospheric pressure or more and steam having a pressure of the atmospheric pressure or more can be generated. This steam condensate may be used as the low-low-pressure steam condensate to be supplied to the step a. The temperature of the steam condensate having the atmospheric pressure is about 100° C. The temperature of the steam condensate having 2 bar or more is 120° C. or more.

Embodiment 1.2: A Second Embodiment of the Steam Condensate Supplied to the Step a In this embodiment, an amount of the condensation-step-supply steam condensate is set larger than an amount of the low-pressure steam generated in the condensation step. Fluid containing the low-pressure steam and steam condensate is obtained from the condensation step. In other words, a cooling-side outlet fluid of the condenser includes the low-pressure steam generated in the condensation step and steam condensate which has not been vaporized in the condensation step.

In addition, the following step d is performed.

d) A step of separating the fluid containing the low-pressure steam and the steam condensate (the cooling-side outlet fluid of the condenser) obtained from the condensation step into the low-pressure steam and the steam condensate.

In order to perform the step d, an appropriate gas-liquid separator may be used. The steam condensate separated in the step d is entirely or partially used as the steam condensate whose temperature is higher than 90° C. to be supplied to the step a. Before the steam condensate separated in the step d is returned to the condenser as the condensation-step-supply steam condensate in the step c, make-up water may be added to the steam condensate separated in the step d. Note that the low-pressure steam separated in the step d may be appropriately used as a heat source.

The temperature and the pressure of the low-pressure steam and the steam condensate separated in the step d may be the same as the temperature and the pressure explained above about the low-pressure steam generated in the condensation step. Therefore, the temperature of the steam condensate supplied to the step a (the steam condensate separated in the step d) is typically a saturation temperature of water at the abovementioned pressure of the low-pressure steam generated in the condensation step.

Embodiment 1.3: A Third Embodiment of the Steam Condensate Whose Temperature is Higher than 90° C.

In this embodiment, in the high-pressure decomposition step, the urea synthesis solution generated in the synthesis step is heated by using the medium-pressure steam as a heat source and medium-pressure steam condensate is obtained. This medium-pressure steam condensate is entirely or partially used as the steam condensate to be supplied to the step a. The medium-pressure steam condensate obtained in the high-pressure decomposition step may be used as, for example, a heat source in the purification step, and thereafter may be supplied to the step a as the steam condensate whose temperature is higher than 90° C.

Alternatively, instead of the medium-pressure steam condensate, medium-low-pressure steam condensate may be used as the steam condensate to be supplied to the step a.

The temperature of the steam condensate (the medium-pressure steam condensate or the medium-low-pressure steam condensate) to be supplied to the step a is typically a saturation temperature of water at the abovementioned pressure of the medium-pressure steam condensate or the medium-low-pressure steam condensate. After being appropriately cooled by heat exchange with another fluid to, for example, about 160° C., the medium-pressure steam condensate or the medium-low-pressure steam condensate may be supplied to the step a. Consequently, heat can be recovered from the medium-pressure steam condensate or the medium-low-pressure steam condensate.

Embodiment 2.1: A First Embodiment of Another Fluid to be Supplied to the Step a In this embodiment, as the "another fluid" which is heat-exchanged with the steam condensate whose temperature is higher than 90° C. in the step a, raw material ammonia to be supplied to at least one step selected from among the synthesis step, the high-pressure decomposition step and the condensation step is entirely or partially used. In other words, the raw material ammonia is preheated by the heat exchange with the steam condensate whose temperature is higher than 90° C. The temperature of the raw material ammonia is, for example, about 40° C.

Embodiment 2.2: A Second Embodiment of Another Fluid to be Supplied to the Step a In this embodiment, the purification step, the concentration step and the granulation step are performed. As the "another fluid" which is heat-exchanged with the steam condensate whose temperature is higher than 90° C. in the step a, air to be supplied to the granulation step is entirely or partially used. In other words, the air (typically having the atmospheric temperature) to be supplied to the granulation step is heated by the heat exchange with the steam condensate whose temperature is higher than 90° C.

Embodiment 3.1: A First Embodiment of the Heat Recovery Target Fluid

In this embodiment, the recovering step is performed. In the step b, an absorption medium, which has absorbed at least one gas of the gas I and the gas II, is entirely or partially used as the heat recovery target fluid. This heat recovery target fluid and the steam condensate obtained from the step a are heat-exchanged. Consequently, the cooling in the recovering step (cooling of at least one of the gas I and the gas II) is performed together with the heating in the step b (the heating of the steam condensate supplied to the step b).

Embodiment 3.2: A Second Embodiment of the Heat Recovery Target Fluid

In this embodiment, the recovering step is performed. The cooling (cooling of an absorption medium that has absorbed at least one gas of the gas I and the gas II) in the recovering step is performed by heat exchange with hot water. In the step b, the hot water after being used as a cooling source for the cooling in the recovering step is entirely or partially used as the heat recovery target fluid. This hot water and the steam condensate obtained from the step a are heat-exchanged. Consequently, the heating in the step b (heating of the steam condensate supplied to the step b) is performed. Heat is recovered from the hot water after being used as the cooling source for the cooling in the recovering step.

Embodiment 3.3: A Third Embodiment of the Heat Recovery Target Fluid

In this embodiment, the purification step, the concentration step, the low-low-pressure fluid generation step and the following step e are performed.

e) A step of, by cooling the entire or a part of the low-low-pressure steam, which is generated in the low-low-pressure fluid generation step, condensing this low-low-pressure steam and obtaining steam condensate.

The cooling in the step e is performed together with the heating in the step b by heat-exchanging, in the step b, the entire or a part of the low-low-pressure steam, which is generated in the low-low-pressure generation step, with the steam condensate obtained from the step a.

Therefore, in the second heat exchange structure, the low-low-pressure steam can be heat-exchanged with the steam condensate obtained from the first heat exchange structure. Consequently, it is possible to perform heating in the second heat exchange structure (heating of the steam condensate obtained from the first heat exchange structure)

and condense the low-low-pressure steam by cooling the low-low-pressure steam and obtain steam condensate.

For example, the temperature of the low-low-pressure steam supplied to the step e is about 100 to 150° C. (a saturation temperature at the pressure of the low-low-pressure steam). When subcooling is not performed in the step e, the temperature of the steam condensate discharged from the step e is also the saturation temperature. If subcooling is performed in the step e, the temperature of the steam condensate becomes lower than the saturation temperature.

In this embodiment, it is preferable to perform the following step f.

f) A step of returning the steam condensate obtained from the step e to the low-low-pressure fluid generation step, wherein the steam condensate obtained from the step e is transferred to the low-low-pressure fluid generation step by the own weight of this steam condensate.

In order to perform the step f, a line for returning the steam condensate obtained by condensing the low-low-pressure steam in the second heat exchange structure to the low-low-pressure fluid generating apparatus (that is, a line connecting the high-temperature side outlet of the second heat exchange structure and the inlet of the low-low-pressure fluid generating apparatus) may be used. It is possible to transfer, through this line, the steam condensate obtained by condensing the low-low-pressure steam in the second heat exchange structure to the low-low-pressure fluid generating apparatus by the own weight of this steam condensate.

The transfer may be performed as follows. The low-low-pressure steam condensate generated in the low-low-pressure fluid generation step is received in a container or a tube. A liquid surface of the low-low-pressure steam condensate is formed in the container or the tube. In the step e, the low-low-pressure steam is condensed in a position higher than the level of this liquid surface. Thus condensed steam condensate is directed to the container or the tube used in the low-low-pressure fluid generation step.

When the pressure of the steam condensate obtained from the step e is higher than the atmospheric pressure (for example, an operation pressure in the low-low-pressure fluid generation step is 2 bar or more), instead of the step f, the steam condensate obtained from the step e may be sent to a tank, which stores steam condensate having the atmospheric pressure, by a pressure difference. When the pressure of the steam condensate obtained from the step e is the atmospheric pressure, instead of the step f, the steam condensate obtained from the step e may be pressurized by a pump and returned to the low-low-pressure fluid generation step or may be discharged to the outside of the apparatus for urea production.

[Others]

The process for urea production may include the following step g.

g) A step of heat-exchanging the steam condensate heated in the step b with the low-pressure steam generated in the condensation step to heat this steam condensate before being supplied to the condensation step as the concentration-step-supply steam condensate.

In order to perform the step g, an appropriate heat exchange structure may be used. A low-temperature side of the heat exchange structure that performs the step g may be disposed in a line connecting the low-temperature side outlet of the second heat exchange structure and a condensation-step-supply steam condensate inlet (a cooling-side inlet) of the condenser. The low-pressure steam generated in the condensation step may be supplied to a high-temperature side of the heat exchange structure that performs the step g.

When the temperature of the condensation-step-supply steam condensate is lower, an amount of the steam condensate necessary for generating the low-pressure steam in the condensation step decreases. In this case, an amount of the steam condensate cooled in the step a and heated in the step b may decrease and a heat quantity of heat recovery by the step b may decrease. In order to avoid such a decrease in the heat recovery amount, the steam condensate heated in the step b may be supplied to the condensation step after being heated in the step g.

Since the urea synthesis reaction also progresses in the condensation step, the condensation step and the synthesis step may be performed in a single pressure vessel. Therefore, it is possible to use a single pressure vessel in which a condenser and a synthesis reactor are integrated.

Process Example

The present invention will be described below in detail with reference to drawings, but the present invention is not limited thereto. In the drawings, "MP STM" means medium-pressure steam, "LP STM" means low-pressure steam, "LLP STM" means low-low-pressure steam, "MP SC" means medium-pressure steam condensate, "LP SC" means low-pressure steam condensate, and "LLP SC" means low-low-pressure steam condensate. In FIGS. 1-4, solid lines represent steam and broken lines represent steam condensate. Strictly speaking, when steam condensate having a high pressure is reduced in pressure, the steam condensate changes into a two-phase flow of steam and steam condensate. Herein, however, such a two-phase flow is indicated by broken lines as well.

A Process Example of the Embodiment 1.1

An example of a process (a steam/steam condensate system) of the embodiment 1.1 is explained with reference to FIG. 1. In this example, low-low-pressure steam condensate is used as the steam condensate whose temperature is higher than 90° C. in the step a. In this example, ammonia preheater E is used as the apparatus (the first heat exchange structure) that performs the step a. In other words, this example conforms to the embodiment 2.1 as well.

The low-pressure steam condensate in line 1 derives from medium-pressure steam condensate obtained by condensing medium-pressure steam in a high-pressure decomposer. Specifically, the medium-pressure steam condensate from the high-pressure decomposer is reduced in pressure by, for example, a pressure reducing valve (not shown) to become low-pressure steam and low-pressure steam condensate. The low-pressure steam and the low-pressure steam condensate are subjected to gas-liquid separation in a vessel (not shown) and low-pressure steam condensate is obtained.

The low-pressure steam condensate in line 1 is heated by a process fluid in condenser A (used for recovery of condensation heat) to become low-pressure steam.

A part of the low-pressure steam withdrawn from condenser A to line 2 is sent to purification apparatus B via line 3 and used as a heat source. Another part of the low-pressure steam in line 2 is sent to concentration apparatus C via line 4 and used as a heat source. The remaining part of the low-pressure steam in line 2 may be used as appropriate as a heat source other than the abovementioned heating sources. However, this heat source is not shown in FIG. 1.

Low-pressure steam condensates obtained by condensing the low-pressure steam are withdrawn from purification apparatus B and concentration apparatus C respectively to line 5 and line 6. The low-pressure steam condensates join together and are sent to low-low-pressure fluid generating apparatus D via line 7.

Low-low-pressure fluid generating apparatus D reduces in pressure the low-pressure steam condensate to generate low-low-pressure steam condensate and low-low-pressure steam, performs gas-liquid separation of the low-low-pressure steam condensate and the low-low-pressure steam in a vessel, obtains low-low-pressure steam in line 8, and obtains low-low-pressure steam condensate in line 9 (both of the low-low-pressure steam and the low-low-pressure steam condensate are, for example, at 140° C.).

The low-low-pressure steam in line 8 is appropriately used. For example, the low-low-pressure steam in line 8 is sent to an ammonia preheater (not shown in FIG. 1, but shown in FIG. 5 with a reference "N") and heats the raw material ammonia.

The low-low-pressure steam condensate in line 9 is sent to ammonia preheater E as the "steam condensate whose temperature is higher than 90° C." in the step a and cooled to 90° C. or less (for example, 50° C.) by heat exchange with the raw material ammonia (the step a). The cooled low-low-pressure steam condensate is withdrawn to line 10. Ammonia preheater E may be disposed upstream of ammonia preheater N in relation to the flow direction of the raw material ammonia.

The low-low-pressure steam condensate in line 10 is divided into lines 12 and 13. The low-low-pressure steam condensate in line 12 is discharged to the outside of the apparatus for urea production (for example, toward the boiler water supply adjusting apparatus). The low-low-pressure steam condensate may be further cooled by cooling water (utility) before being discharged to the outside of the apparatus for urea production. When the pressure of the low-low-pressure steam condensate is higher than the atmospheric pressure to some extent, the low-low-pressure steam condensate may be further reduced in pressure before being discharged to the outside of the apparatus for urea production and stored once in a tank under the atmospheric pressure and then discharged to the outside of the apparatus for urea production. The low-low-pressure steam condensate in line 13 is supplied to heat exchanger F (the second heat exchange structure) that performs the step b.

In heat exchanger F that performs the step b, the low-low-pressure steam condensate supplied from line 13 (that is, the steam condensate obtained from the step a) is heated by heat exchange with the heat recovery target fluid. The heat recovery target fluid, for example, conforms to at least one of the embodiments 3.1 to 3.3.

The low-low-steam condensate heated by heat exchanger F is discharged to line 11 from heat exchanger F. The low-low-pressure steam condensate in line 11 is sent to condenser A as the condensation-step-supply steam condensate. Note that, however, the low-low-pressure steam condensate in line 11 is supplied to a vessel (not shown) and is sent from the vessel to condenser A. It should be understood that, in FIG. 1, the vessel is included in a block indicating condenser A. Although not shown in FIG. 1, it should be understood that a pressurizing device for pressuring the steam condensate is provided in line 9, 10, 13 or 11. Even if the steam condensate pressurized by the pressurizing device has a pressure equivalent to the pressure of the low-pressure steam condensate, the temperature of the steam condensate does not substantially change before and after the pressurizing device. In order to distinguish the steam condensate pressurized by the pressurizing device from the low-pressure steam condensate generated by condensing the low-pressure steam, the steam condensate pressurized by the pressurizing device is also indicated as "low-low-pressure steam condensate". For example, the low-low-pressure steam condensate (line 11) can be pressurized to the same pressure as the pressure of the low-pressure steam condensate (line 1). Then, these steam condensates (lines 1 and 11) may be joined and supplied to condenser A as the condensation-step-supply steam condensate.

Process Example of the Embodiment 1.2

An example of a process (a steam/steam condensate system) of the embodiment 1.2 is explained with reference to FIG. 2. Explanation is omitted about points which are common to the example shown in FIG. 1. In this example, a fluid containing low-pressure steam and steam condensate is generated from the condensation step as a cooling-side outlet fluid of condenser A. The condenser cooling-side outlet fluid is separated into the low-pressure steam and the steam condensate (the step d). The steam condensate separated in the step d is used as the steam condensate whose temperature is higher than 90° C. in the step a.

The cooling-side outlet fluid of condenser A is separated by a gas-liquid separator (a vessel not shown in FIG. 2), the low-pressure steam is withdrawn to line 2, and the low-pressure steam condensate is withdrawn to line 20 (both of the low-pressure steam and the low-pressure steam condensate are, for example, at 160° C.).

The low-low-pressure steam condensate generated in low-low-pressure fluid generating apparatus D is supplied to condenser A as the condensation-step-supply steam condensate via line 29. A not-shown pressurizing device is provided in line 29 to pressurize this steam condensate.

The low-pressure steam condensate in line 20 is sent to ammonia preheater E as the steam condensate whose temperature is higher than 90° C. in the step a and cooled to 90° C. or less (for example, 50° C.) by heat exchange with the raw material ammonia (the step a). The cooled low-pressure steam condensate is withdrawn to line 24.

The low-pressure steam condensate in line 24 is divided into lines 22 and 23. The low-pressure steam condensate in line 22 is discharged to the outside of the apparatus for urea production (for example, toward an ammonia plant). The low-pressure steam condensate in line 23 is supplied to heat exchanger F that performs the step b.

In heat exchanger F that performs the step b, the low-pressure steam condensate supplied from the line 23, that is, the steam condensate obtained from the step a is heated by heat exchange with the heat recovery target fluid. The heat recovery target fluid is, for example, a fluid conforming to at least one of the embodiments 3.1 to 3.3.

The low-pressure steam condensate heated by heat exchanger F is discharged to line 21 from heat exchanger F. The low-pressure steam condensate in line 21 is sent to condenser A as the condensation-step-supply steam condensate. Although not shown in FIG. 2, it should be understood that a pressurizing device for pressurizing steam condensate is provided in line 20, 24, 23 or 21.

A Process Example of the Embodiment 1.3

An example of a process (a steam/steam condensate system) of the embodiment 1.3 is explained with reference to FIG. 3. Explanation is omitted about points which are common to the example shown in FIG. 2. In this example, in the high-pressure decomposition step, the medium-pressure steam is used as a heat source to heat the urea synthesis solution generated in the synthesis step and obtain the medium-pressure steam condensate. The medium-pressure steam condensate is used as the "steam condensate whose temperature is higher than 90° C." in the step a.

The medium-pressure steam condensate (line 35) obtained from the high-pressure decomposer is divided into line 1 and line 36. The medium-pressure steam condensate in line 1 is reduced in pressure by, for example, a pressure reducing valve (not shown) to become low-pressure steam and low-pressure steam condensate. The low-pressure steam and the low-pressure steam condensate are subjected to gas-liquid separation by a vessel (not shown). The low-pressure steam condensate is supplied to condenser A.

The medium-pressure steam condensate in line 36 is sent to ammonia preheater E as the steam condensate whose temperature is higher than 90° C. in the step a and cooled to 90° C. or less (for example, 50° C.) by heat exchange with the raw material ammonia (the step a).

Figure 2:
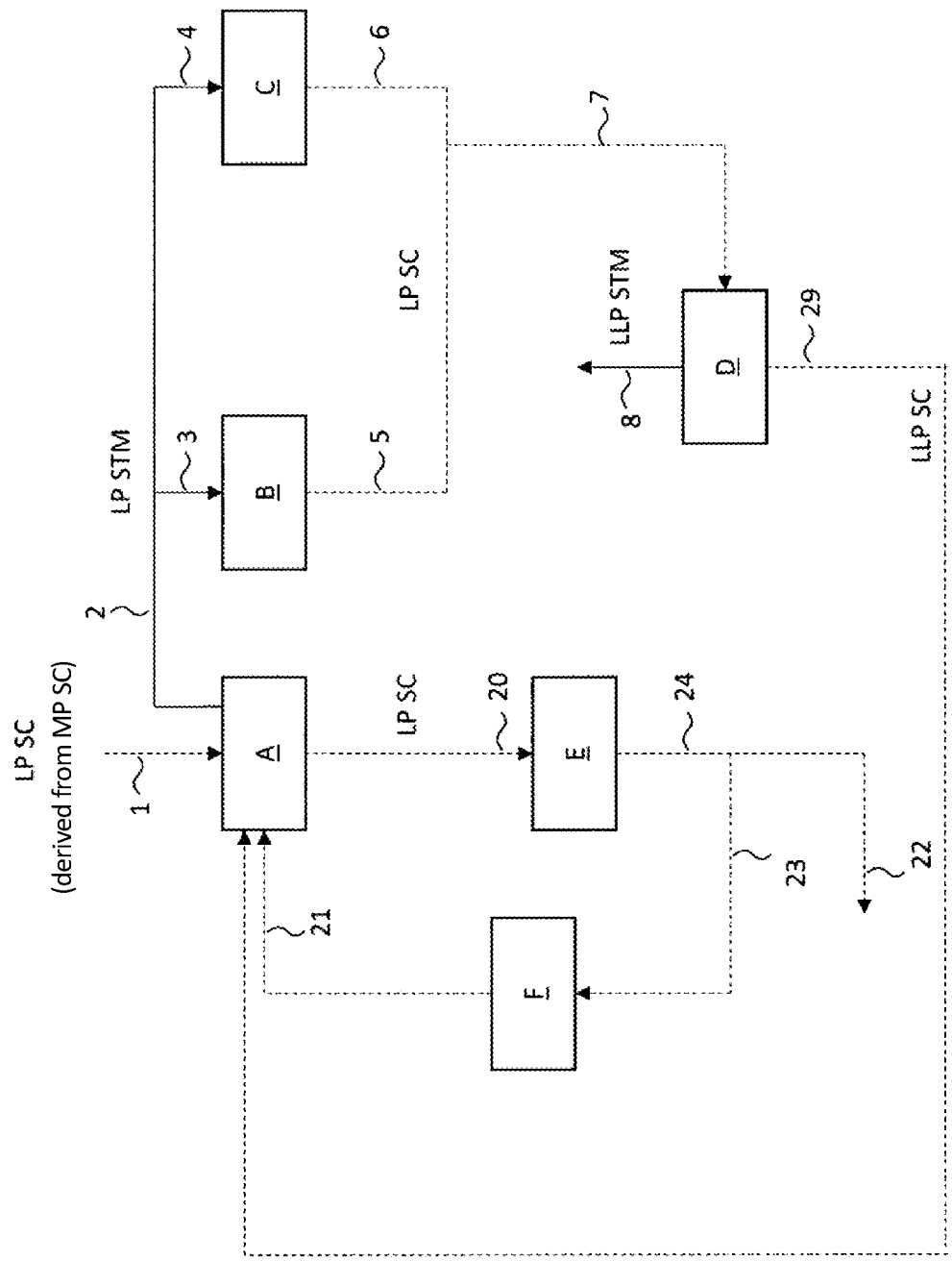
FIG. 2 is a schematic diagram for explaining another process example of the steam/steam condensate system according to the present invention.
Figure 3:
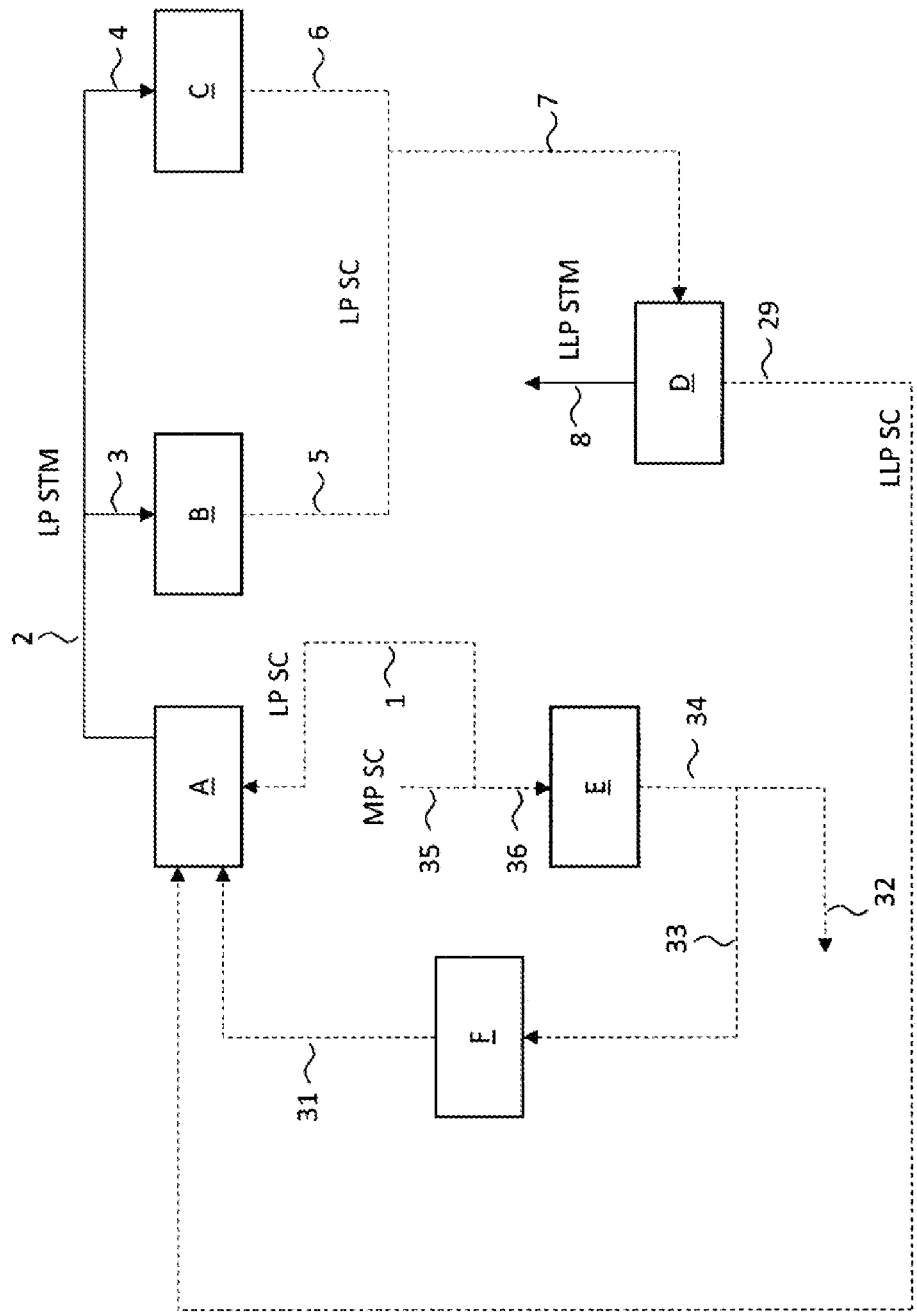
FIG. 3 is a schematic diagram for explaining a further process example of the steam/steam condensate system according to the present invention.

Ammonia preheater E, heat exchanger F and lines 31 to 34 are the same as ammonia preheater E, heat exchanger F and lines 21 to 24 in the embodiment shown in FIG. 2 except that steam condensate flowing therethrough is not the low-pressure steam condensate but is the medium-pressure steam condensate. However, when the medium-pressure steam condensate in line 31 is supplied to condenser A as the condensation-step-supply steam condensate, the medium-pressure steam condensate is subjected to operation such as pressure reduction and gas-liquid separation as necessary.

Figure 4:
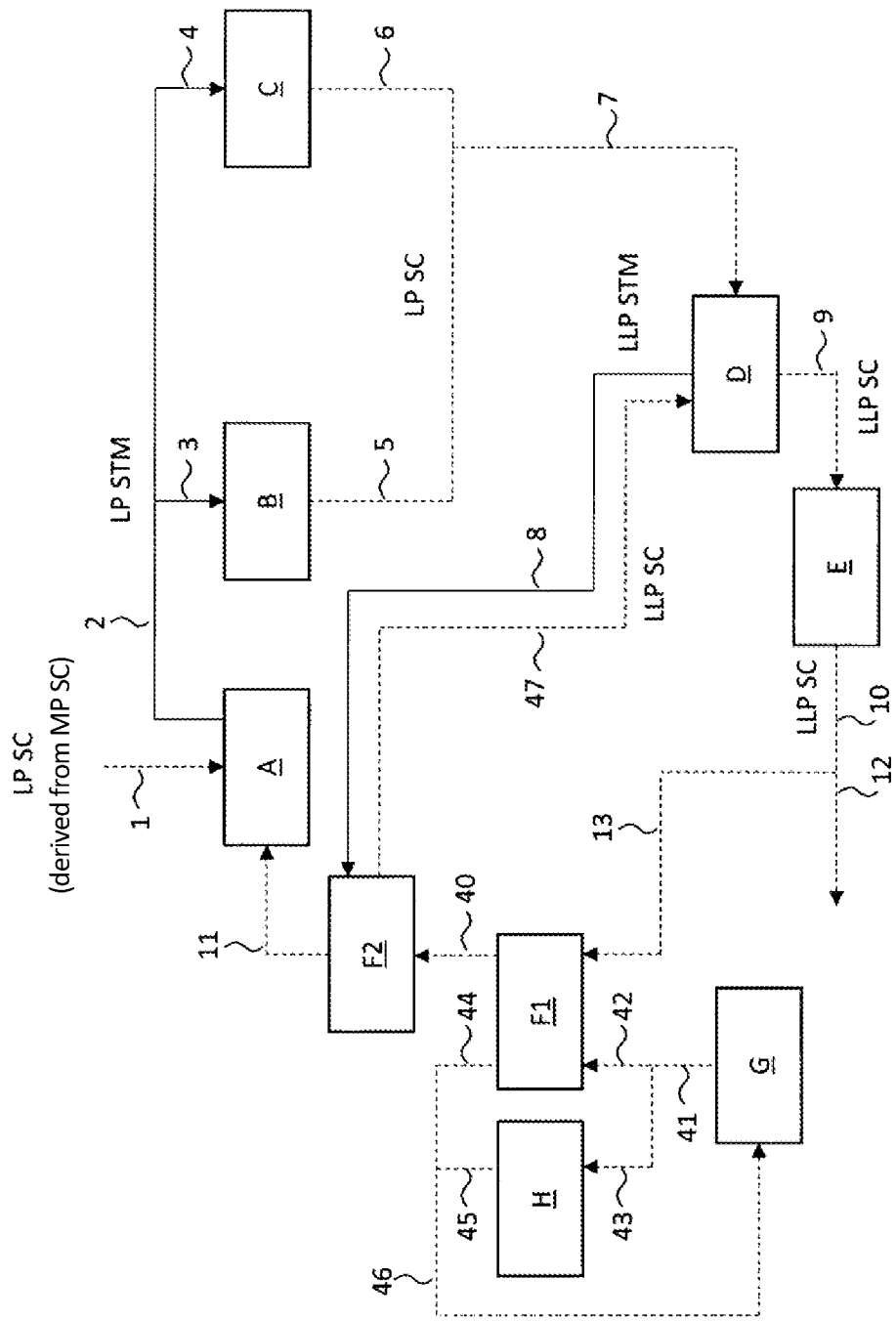
FIG. 4 is a schematic diagram for explaining a still further process example of the steam/steam condensate system according to the present invention.

[A process example in which the embodiment 3.2 and the embodiment 3.3 are combined] An example of another process (steam/steam condensate system) is explained with reference to FIG. 4. This example is an example in which apparatuses for the step b (heat exchanger F and apparatus associated with heat exchanger F) in the process example shown in FIG. 1 are explained more in detail. Explanation is omitted about points which are common to the example shown in FIG. 1. In this example, as the heat exchanger (the second heat exchange structure) that performs the step b, heat exchanger F1 (see the embodiment 3.2) and heat exchanger F2 (see the embodiment 3.3) are used. In this way, a plurality of the second heat exchange structures may be present or only one second heat exchange structure may be present. The same applies to the first heat exchange structure.

The low-low-pressure steam condensate (for example, 50° C.) in line 13 is heated by heat exchanger F1 and discharged to line 40 (for example, 100° C.). On the other hand, the hot water (for example, 100° C.) after being used as the cooling source in the recovering step is discharged to line 41 from recovering apparatus G that performs the recovering step. Subsequently, the hot water in line 41 is divided into line 42 and line 43. The hot water in line 42 is supplied to heat exchanger F1 as the heat recovery target fluid, cooled (subjected to heat-recovery), and discharged to line 44. In this way, the low-low-pressure steam condensate in line 13 and the hot water in line 42 are heat-exchanged in heat exchanger F1 (the step b).

The hot water in line 43 is cooled by heat exchange with cooling water (utility) in cooler H and discharged to line 45. A line for this cooling water is not shown in FIG. 4. The hot water in line 44 and the hot water in line 45 join in line 46, are returned to recovering apparatus G, and used to cool the process fluid in the recovering step. The temperature of the hot water returned to recovering apparatus G is, for example, 90° C. The pressure of this hot water is, for example, 15 bar. The cooling water (utility) after being used for the cooling in cooler H is generally appropriately cooled again on the outside of cooler H.

It is possible to adjust a heat exchange amount in heat exchanger F1 by dividing the hot water in line 41 into lines 42 and 43.

The low-low-pressure steam condensate in line 40 (the steam condensate obtained from the step a) is further heated in heat exchanger F2 and discharged to line 11 (for example, 120° C.). On the other hand, the low-low-pressure steam (for example, 140° C.) in line 8 is supplied to heat exchanger F2 as the heat recovery target fluid, cooled (subjected to heat recovery), and condensed (the step e). The low-low-pressure steam condensate obtained by this condensation is discharged to line 47. In this way, the low-low-pressure steam condensate in line 40 and the low-low-pressure steam in line 8 are heat-exchanged.

The low-low-pressure steam condensate in line 11 is returned to condenser A as the condensation-step-supply steam condensate.

The low-low-pressure steam condensate in line 47 is transferred to low-low-pressure fluid generating apparatus D by the own weight of this low-low-pressure steam condensate. Therefore, a position where the low-low-pressure steam in line 8 is condensed in the step e in heat exchanger F2 is set higher than (that is, above in the vertical direction) a liquid surface in apparatus D (a liquid surface of the low-low-pressure steam condensate generated by reducing the low-pressure steam condensate in line 7 in pressure).

A pressurizing device may be appropriately used in this embodiment as well.

Process Example of the Process for Urea Production

Figure 5:
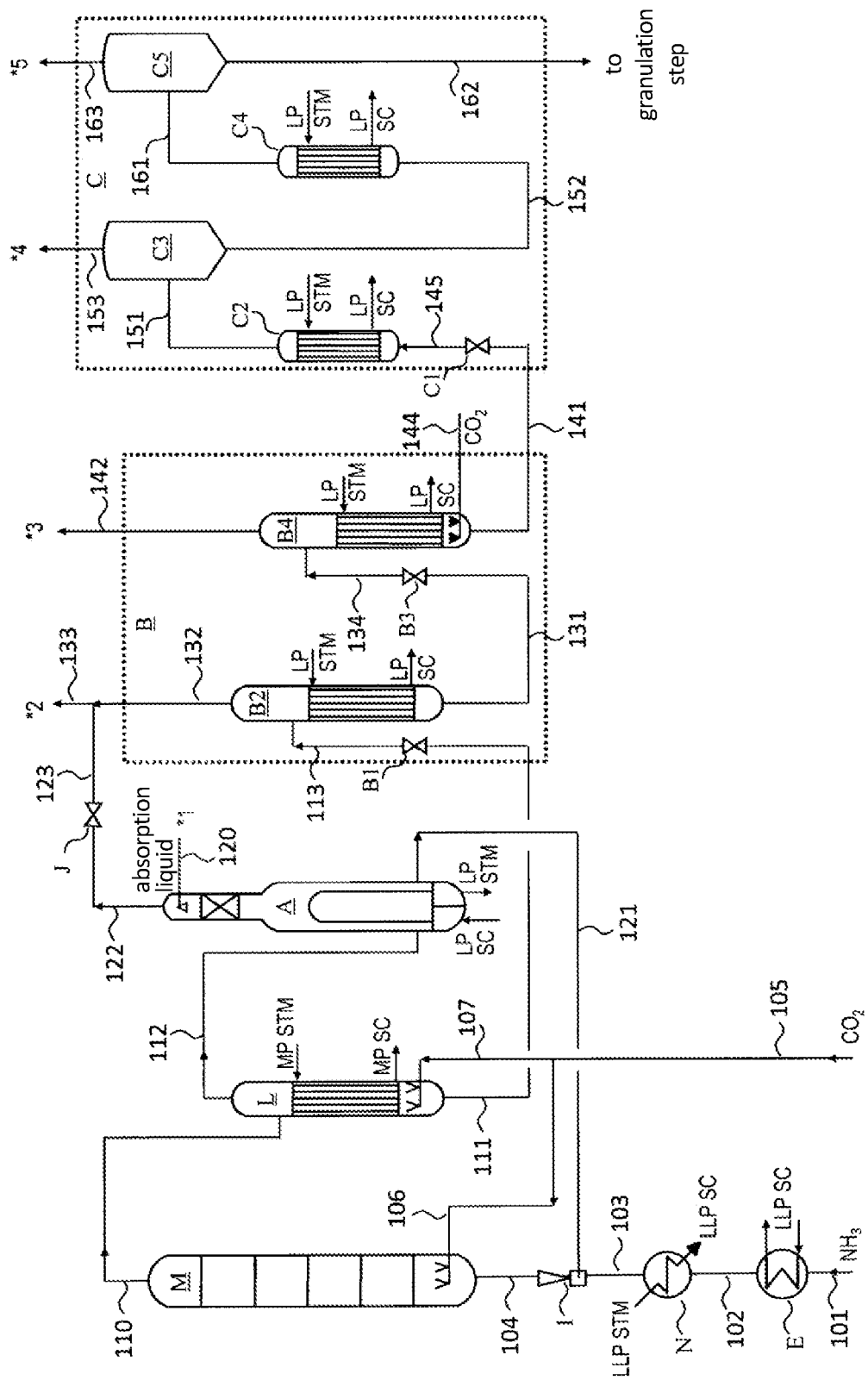
FIG. 5 is a process flow diagram showing an example of a schematic configuration of a urea production apparatus.

As shown in FIG. 5, raw material ammonia appropriately pressurized by a pump (not shown) is supplied to synthesis reactor M via lines 101, 102, 103 and 104. Raw material carbon dioxide is supplied to synthesis reactor M via lines 105 and 106. The raw material ammonia (line 101) is heated by heat exchange with low-low-pressure steam condensate in heat exchanger (ammonia preheater) E. The heated raw material ammonia (line 102) is then heated by heat exchange with low-low-pressure steam in heat exchanger (ammonia preheater) N. The low-low-pressure steam is condensed by the heat exchanger N to become low-low-pressure steam condensate. Thereafter, the heated raw material ammonia (line 103) can be used as a driving fluid for ejector I. Although not shown in FIG. 5, a heat exchanger may be added to line 103 to further heat the raw material ammonia through heat exchange with low-pressure steam.

A urea synthesis solution is sent from synthesis reactor M to high-pressure decomposer L via line 110. In high-pressure decomposer L, the urea synthesis solution is heated in a heating section (a heat exchange structure) which performs heating by using medium-pressure steam. The medium-pressure steam becomes medium-pressure steam condensate and is withdrawn from this heating section. Carbon dioxide is supplied to the bottom of high-pressure decomposer L as a stripping gas via lines 105 and 107.

High-pressure decomposition outlet gas is introduced into condenser A from high-pressure decomposer L via line 112. Further, the urea synthesis solution, from which the high-pressure decomposition outlet gas has been separated, is sent to purification apparatus B via line 111.

The high-pressure decomposition outlet gas introduced into condenser A is absorbed by absorption liquid (an absorption medium) introduced from line 120, and condenses. The obtained condensed liquid is pressurized by ejector I after flowing through line 121, and recycled to synthesis reactor M from line 104. Gas which remains uncondensed (condenser outlet gas) is withdrawn from line 122 and reduced in pressure by pressure reducing valve J. Low-pressure steam condensate is introduced into condenser A as a cooling source. The low-pressure steam condensate is heated by the internal fluid (process fluid) of condenser A to generate low-pressure steam.

Purification apparatus B includes pressure reducing valve B1, medium-pressure decomposer B2, pressure reducing valve B3, and low-pressure decomposer B4. The urea synthesis solution from line 111 is reduced in pressure by pressure reducing valve B1 and sent to the medium-pressure decomposer B2, which performs a medium-pressure decomposition step, via line 113. The urea synthesis solution (which may be a gas-liquid two-phase flow) introduced into the medium-pressure decomposer B2 from line 113 is heated in a heating section (a heat exchange structure), which performs heating by using low-pressure steam, of the medium-pressure decomposer B2. The low-pressure steam becomes low-pressure steam condensate and is withdrawn from this heating section.

Medium-pressure decomposition outlet gas is withdrawn from line 132. A urea synthesis solution, from which the medium-pressure decomposition outlet gas has been separated, is withdrawn from line 131, reduced in pressure by pressure reducing valve B3, and introduced from line 134 into low-pressure decomposer B4 which performs a low-pressure decomposition step. Carbon dioxide is supplied from line 144 to low-pressure decomposer B4 in order to promote decomposition of carbamate.

The urea synthesis solution (which may be a gas-liquid two-phase flow) introduced into low-pressure decomposer B4 from line 134 is heated in a heating section (a heat exchange structure), which performs heating by using low-pressure steam, of low-pressure decomposer B4. Low-pressure decomposition outlet gas is withdrawn from line 142. A urea synthesis solution, from which the low-pressure decomposition outlet gas has been separated, is withdrawn from line 141 and sent to concentration apparatus C.

Concentration apparatus C includes pressure reducing valve C1, heater C2, gas-liquid separator C3, heater C4, and gas-liquid separator C5. The urea synthesis solution from line 141 is reduced in pressure by pressure reducing valve C1 and introduced into heater C2 from line 145. In this heater (in particular, a heat exchange structure of the heater), the urea synthesis solution is heated by low-pressure steam, and low-pressure steam condensate is generated. The heated urea synthesis solution becomes a gas-liquid two-phase flow and is introduced into gas-liquid separator C3 from line 151. The gas phase is withdrawn to line 153 and the liquid phase (a urea synthesis solution in which urea has been further concentrated) is withdrawn to line 152.

The urea synthesis solution in line 152 is introduced into heater C4. In this heater (in particular, a heat exchange structure of the heater), the urea synthesis solution is heated by low-pressure steam, and low-pressure steam condensate is generated. The heated urea synthesis solution becomes a gas-liquid two-phase flow and is introduced into gas-liquid separator C5 from line 161. The gas phase is withdrawn to line 163 and the liquid phase (a urea synthesis solution in which urea has been further concentrated) is withdrawn to line 162. The liquid phase is sent to a granulation step.

The condenser outlet gas (line 122; after pressure reduction, line 123) withdrawn from condenser A is the abovementioned gas I. The medium-pressure decomposition outlet gas (line 132) and the low-pressure decomposition outlet gas (line 142) respectively withdrawn from the medium-pressure decomposer B2 and the low-pressure decomposer B4 are the abovementioned gas II. In the recovering step, ammonia, carbon dioxide and water contained in these gases can be recovered. In such recovery processing, the gas can be absorbed and condensed into an absorption medium and the absorption medium, which has absorbed the gas, can be simultaneously cooled. As the absorption medium, an absorption medium publicly known in the field of the process for urea production, such as water (which may contain urea, ammonia, carbon dioxide and ammonium carbamate) may be appropriately used. In addition, water (steam) contained in the gases withdrawn from gas-liquid separator C3 and gas-liquid separator C5 can be recovered.

Figure 6:
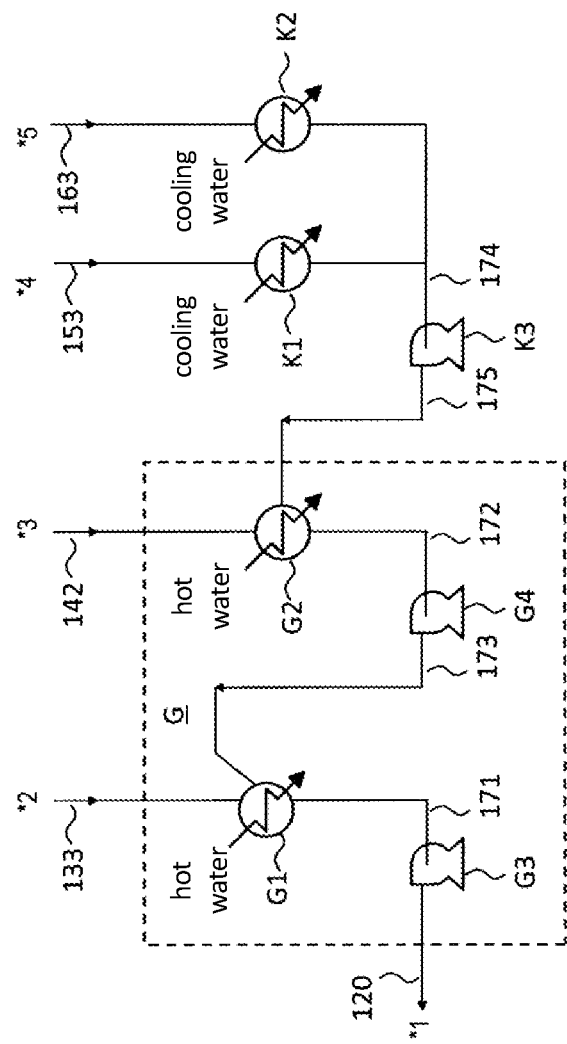
FIG. 6 is a process flow diagram showing an example of a schematic configuration of a recovering apparatus.

An example of such processing is explained below. As shown in FIG. 5, a gaseous mixture (line 133) is obtained by mixing the medium-pressure decomposition outlet gas (line 132) and the condenser outlet gas (line 123) after being reduced in pressure by pressure reducing valve J. As shown in FIG. 6, recovering apparatus G includes medium-pressure absorber G1, low-pressure absorber G2 and pumps G3 and G4. In medium-pressure absorber G1, the gaseous mixture (line 133) is absorbed and condensed in liquid supplied from line 173 and this liquid is simultaneously cooled by using hot water to obtain recovered liquid in line 171. The recovered liquid is pressurized by pump G3 and supplied from line 120 to condenser A as an absorption medium.

In low-pressure absorber G2, the low-pressure decomposition outlet gas (line 142) is absorbed and condensed in liquid supplied from line 175 and this liquid is simultaneously cooled by using hot water to obtain recovered liquid in line 172. The recovered liquid is pressurized by pump G4 and sent from line 173 to medium-pressure absorber G1 as an absorption medium.

The gas in line 153 withdrawn from gas-liquid separator C3 is sent to heat exchanger K1. The gas in line 163 withdrawn from gas-liquid separator C5 is sent to heat exchanger K2. These gases are respectively cooled and condensed in these heat exchangers. Condensed water (line 174) is pressurized by pump K3 and sent from line 175 to low-pressure absorber G2 as an absorption medium. An appropriate cooling medium, such as cooling water (utility), may be used for the cooling in heat exchangers K1 and K2.

Examples in which the abovementioned embodiments are applied to the apparatus for urea production having the configuration shown in FIGS. 5 and 6 are explained below.

Embodiment 1.1

In the low-low-pressure generation step, at least a part of the low-pressure steam condensate obtained from one or more apparatus among purification apparatus B and concentration apparatus C (specifically, medium-pressure decomposer B2, low-pressure decomposer B4, heater C2 and heater C4) is reduced in pressure by a pressure reducing valve (not shown) and separated by a gas-liquid separator (not shown) to generate low-low-pressure steam condensate and low-low-pressure steam. In the embodiment 1.1, this low-low-pressure steam condensate is used as the steam condensate whose temperature is higher than 90° C. in the step a.

Embodiment 1.2

In the embodiment 1.2, by setting a flow rate of the condensation-step-supply steam condensate larger than an amount, on a mass flow rate basis, of the low-pressure steam generated in condenser A, a fluid containing low-pressure steam and low-pressure steam condensate is obtained from condenser A as the cooling-side outlet fluid of condenser A. This fluid is separated into the low-pressure steam and the steam condensate by using the gas-liquid separator (not shown) (the step d). The steam condensate separated in the step d is used as the steam condensate whose temperature is higher than 90° C. in the step a.

Embodiment 1.3

In the Embodiment 1.3, the medium-pressure steam is used as a heat source in high-pressure decomposer L to obtain medium-pressure steam condensate by condensing this medium-pressure steam. This medium-pressure steam condensate is used as the steam condensate whose temperature is higher than 90° C. in the step a.

Embodiment 2.1

In the embodiment 2.1, raw material ammonia 101 is used as the fluid to be heat-exchanged with the steam condensate whose temperature is higher than 90° C. in the step a. The heat exchange in the step a is performed in ammonia preheater E.

Embodiment 2.2

In the granulation step, granular solid urea is produced from the urea synthesis solution in line 162 by using heated air. In the embodiment 2.2, air to be supplied to the granulation step is used as the fluid which is heat-exchanged with the steam condensate whose temperature is higher than 90° C. in the step a. The air is heated by the heat exchange in the step a. The granulating apparatus includes a heat exchanger (not shown) used for this heat exchange.

Embodiment 3.1

In the embodiment 3.1, an absorption medium, which has absorbed the gas supplied to the recovering step (the gas in lines 133 and 142), is used as the heat recovery target fluid. The steam condensate obtained from the step a is used as the hot water used for the cooling in medium-pressure absorber G1 and low-pressure absorber G2. In this way, in medium-pressure absorber G1 and low-pressure absorber G2, the gasses in lines 133 and 142 are respectively heat-exchanged with the steam condensate obtained from the step a (the step b). The cooling in the recovery step (the cooling of the gas supplied to the recovering step) is performed by this heat exchange simultaneously with the heating in the step b (the heating of the steam condensate obtained from the step a).

When a condensation temperature in low-pressure absorber G2, to which the gas in line 142 is supplied, is low and it is not easy to heat-exchange this gas with the steam condensate obtained from the step a, the step b is performed in medium-pressure absorber G1 but may not be performed in low-pressure absorber G2. When the step b is not performed in low-pressure absorber G2, for example, cooling water (utility) may be used instead of the hot water as the cooling medium used for the cooling in low-pressure absorber G2.

Embodiment 3.2

In the embodiment 3.2, the hot water after being used as the cooling source for the cooling in the recovering step, that is, the hot water discharged from at least one of medium-pressure absorber G1 and low-pressure absorber G2 is heat-exchanged with the steam condensate obtained from the step a.

About the Step g

In the step g, it is possible to heat-exchange the steam condensate to be supplied to condenser A with the low-pressure steam generated in condenser A in a heat exchanger (not shown) to heat this steam condensate before being supplied to condenser A.

REFERENCE SIGNS LIST

MP STM MEDIUM-PRESSURE STEAM
LP STM LOW-PRESSURE STEAM
LLP STM LOW-LOW-PRESSURE STEAM
MP SC MEDIUM-PRESSURE STEAM CONDENSATE
LP SC LOW-PRESSURE STEAM CONDENSATE
LLP SC LOW-LOW-PRESSURE STEAM CONDENSATE
A CONDENSER
B PURIFICATION APPARATUS
B1, B3 PRESSURE REDUCING VALVE
B2 MEDIUM-PRESSURE DECOMPOSER
B4 LOW-PRESSURE DECOMPOSER
C CONCENTRATION APPARATUS
C1 PRESSURE REDUCING VALVE
C2 HEATER
C3 GAS-LIQUID SEPARATOR
C4 HEATER
C5 GAS-LIQUID SEPARATOR
D LOW-LOW-PRESSURE FLUID GENERATING APPARATUS
E HEAT EXCHANGER THAT PERFORMS STEP A (AMMONIA PREHEATER)
F HEAT EXCHANGER THAT PERFORMS STEP B
F1 HEAT EXCHANGER THAT PERFORMS STEP B (FIRST STAGE)
F2 HEAT EXCHANGER THAT PERFORMS STEP B (SECOND STAGE)
G RECOVERING APPARATUS
G1 MEDIUM-PRESSURE ABSORBER
G2 LOW-PRESSURE ABSORBER
G3, G4 PUMP
H COOLER
I EJECTOR
J PRESSURE REDUCING VALVE
K1, K2 HEAT EXCHANGER
K3 PUMP
L HIGH-PRESSURE DECOMPOSER
M SYNTHESIS REACTOR
N HEAT EXCHANGER (AMMONIA PREHEATER)

The invention claimed is:

1. A process for urea production, comprising:
(i) a synthesis step comprising synthesizing urea from ammonia and carbon dioxide to generate a urea synthesis solution;
(ii) a high-pressure decomposition step of comprising heating the urea synthesis solution generated in the synthesis step, decomposing ammonium carbamate and separating a gaseous mixture containing ammonia and carbon dioxide from the urea synthesis solution; and
(iii) a condensation step comprising absorbing and condensing at least a part of the gaseous mixture obtained in the high-pressure decomposition step in an absorption medium and generating a low-pressure steam from a steam condensate with use of heat generated during the condensation, the process for urea production further comprising:
a) heat-exchanging a steam condensate having a temperature higher than 90° C. with another fluid to cool the steam condensate to 90° C. or less;
b) heat-exchanging the steam condensate obtained from step a) with a further fluid having a temperature lower than a temperature of the low-pressure steam, thereby heating the steam condensate obtained from step a);
g) optionally heat-exchanging the steam condensate heated in step b) with the low-pressure steam generated in the condensation step to heat this steam condensate before providing this steam condensate to the condensation step as the steam condensate for generating the low-pressure steam; and
c) providing the steam condensate obtained from step b) or obtained from step a) when present, to the condensation step as the steam condensate for generating the low-pressure steam.

2. The process for urea production according to claim 1, comprising:
a purification step comprising heating, at a pressure lower than the pressure in the high-pressure decomposition step and higher than atmospheric pressure, the urea synthesis solution after being processed in the high-pressure decomposition step to generate a gas phase and a liquid phase, and by separating the gas phase, obtaining a urea synthesis solution having an increased urea concentration and generating a low-pressure steam condensate, a part of the low-pressure steam generated in the condensation step being used as a heat source for heating the urea synthesis solution after being processed in the high-pressure decomposition step;
a concentration step comprising heating, at a pressure lower than the pressure in the purification step and equal to or lower than the atmospheric pressure, the urea synthesis solution after being processed in the purification step to generate a gas phase and a liquid phase, and by separating the gas phase, obtaining a urea synthesis solution having a further increased urea concentration and generating a low-pressure steam condensate, another part of the low-pressure steam generated in the condensation step being used as a heat source for heating the urea synthesis solution after being processed in the purification step; and
a low-low-pressure fluid generation step comprising reducing in pressure at least a part of the low-pressure steam condensate obtained from one or both of the purification step and the concentration step to a pressure equal to or higher than the atmospheric pressure, generating a low-low-pressure steam condensate and a low-low-pressure steam, wherein
in step a), the low-low-pressure steam condensate is used as the steam condensate having a temperature higher than 90° C.

3. The process for urea production according to claim 2, wherein the pressure equal to or higher than the atmospheric pressure in the low-low-pressure fluid generation step is 2 bar or more.

4. The process for urea production according to claim 1, wherein
an amount of the steam condensate supplied to the condensation step is larger than an amount of the low-pressure steam generated in the condensation step, and a fluid containing the low-pressure steam and a steam condensate is obtained from the condensation step, the process for urea production comprises:
d) separating the fluid containing the low-pressure steam and the steam condensate obtained from the condensation step into the low-pressure steam and the steam condensate, and wherein in step a), the steam condensate separated in step d) is used as the steam condensate having a temperature higher than 90° C.

5. The process for urea production according to claim 1, wherein
in the high-pressure decomposition step, the urea synthesis solution generated in the synthesis step is heated with use of a medium-pressure steam as a heat source, and a medium-pressure steam condensate is obtained, and
in step a), the steam condensate having a temperature higher than 90° C. is one of:
the medium-pressure steam condensate obtained in the high-pressure decomposition step; or
a medium-pressure steam condensate obtained by cooling, through heat exchange, the medium-pressure steam condensate obtained in the high-pressure decomposition step; or
a medium-low-pressure steam condensate obtained in a medium-low-pressure steam generation step comprising reducing in pressure the medium-pressure steam condensate obtained in the high-pressure decomposition step to a medium-low pressure, generating a medium-low-pressure steam and a medium-low-pressure steam condensate; or
a medium-low-pressure steam condensate obtained by cooling, through heat exchange, the medium-low-pressure steam condensate obtained in the medium-low-pressure steam generation step.

6. The process for urea production according to claim 1, wherein, in step a), raw material ammonia to be supplied to at least one step selected from the synthesis step, the high-pressure decomposition step and the condensation step is used as said another fluid.

7. The process for urea production according to claim 1, comprising:
a purification step comprising heating, at a pressure lower than the pressure in the high-pressure decomposition step and higher than atmospheric pressure, the urea synthesis solution after being processed in the high-pressure decomposition step to generate a gas phase and a liquid phase, and by separating the gas phase, obtaining a urea synthesis solution having an increased urea concentration and generating a low-pressure steam condensate, a part of the low-pressure steam generated in the condensation step being used as a heat source for heating the urea synthesis solution after being processed in the high-pressure decomposition step;
a concentration step comprising heating, at a pressure lower than the pressure in the purification step and equal to or lower than the atmospheric pressure, the urea synthesis solution after being processed in the purification step to generate a gas phase and a liquid phase, and by separating the gas phase, obtaining a urea synthesis solution having a further increased urea concentration and generating a low-pressure steam condensate, another part of the low-pressure steam generated in the condensation step being used as a heat source for heating the urea synthesis solution after being processed in the purification step; and a granulation step comprising producing granular solid urea, with use of air, from the urea synthesis solution after being processed in the concentration step, wherein in step a), the air to be supplied to the granulation step is used as said another fluid.

8. The process for urea production according to claim 1, comprising a recovering step comprising absorbing and condensing, in an absorption medium, at least one gas of the following gas I and gas II:
gas I is a gas remaining uncondensed in the condensation step, and
gas II is a gas obtained as a gas phase separated in a purification step when the process for urea production comprises the purification step, and
simultaneously cooling the absorption medium, which has absorbed the at least one gas, to obtain a recovered liquid containing ammonia and carbon dioxide, wherein
the purification step is a step comprising heating, at a pressure lower than the pressure in the high-pressure decomposition step and higher than atmospheric pressure, the urea synthesis solution after being processed in the high-pressure decomposition step to generate a gas phase and a liquid phase, and by separating the gas phase, obtaining a urea synthesis solution having an increased urea concentration and generating a low-pressure steam condensate, a part of the low-pressure steam generated in the condensation step being used as a heat source for heating the urea synthesis solution after being processed in the high-pressure decomposition step,
the absorbing and cooling in the recovering step is performed together with the heating in step b), and
the cooling in the recovering step is performed by heat-exchanging the absorption medium, which has absorbed the at least one gas, with the steam condensate obtained from step a).

9. The process for urea production according to claim 1, comprising a recovering step comprising absorbing and condensing, in an absorption medium, at least one gas of the following gas I and gas II:
gas I is a gas remaining uncondensed in the condensation step, and
gas II is a gas obtained as a gas phase separated in a purification step when the process for urea production comprises the purification step, and
simultaneously cooling the absorption medium, which has absorbed the at least one gas, to obtain a recovered liquid containing ammonia and carbon dioxide, wherein
the purification step is a step comprising heating, at a pressure lower than the pressure in the high-pressure decomposition step and higher than atmospheric pressure, the urea synthesis solution after being processed in the high-pressure decomposition step to generate a gas phase and a liquid phase, and by separating the gas phase, obtaining a urea synthesis solution having an increased urea concentration and generating a low-pressure steam condensate, a part of the low-pressure steam generated in the condensation step being used as a heat source for heating the urea synthesis solution after being processed in the high-pressure decomposition step,
the cooling in the recovering step is performed by heat exchange with hot water, and
the heating in step b) is performed by heat-exchanging the hot water, after being used for the cooling in the recovering step, with the steam condensate obtained from step a).

10. The process for urea production according to claim 1, comprising:
a purification step comprising heating, at a pressure lower than the pressure in the high-pressure decomposition step and higher than atmospheric pressure, the urea synthesis solution after being processed in the high-pressure decomposition step to generate a gas phase and a liquid phase, and by separating the gas phase, obtaining a urea synthesis solution having an increased urea concentration and generating a low-pressure steam condensate, a part of the low-pressure steam generated in the condensation step being used as a heat source for heating the urea synthesis solution after being processed in the high-pressure decomposition step;
a concentration step of comprising heating, at a pressure lower than the pressure in the purification step and equal to or lower than the atmospheric pressure, the urea synthesis solution after being processed in the purification step to generate a gas phase and a liquid phase, and by separating the gas phase, obtaining a urea synthesis solution having a further increased urea concentration and generating a low-pressure steam condensate, another part of the low-pressure steam generated in the condensation step being used as a heat source for heating the urea synthesis solution after being processed in the purification step;
a low-low-pressure fluid generation step comprising reducing in pressure at least a part of the low-pressure steam condensate obtained from one or both of the purification step and the concentration step to a pressure equal to or higher than the atmospheric pressure, generating a low-low-pressure steam condensate and a low-low-pressure steam; and
e) condensing the low-low-pressure steam by cooling the low-low-pressure steam to obtain a steam condensate, wherein
the cooling in step e) is performed together with the heating in step b) by heat-exchanging the low-low-pressure steam with the steam condensate obtained from step a).

11. The process for urea production according to claim 10, comprising
f) returning the steam condensate obtained from step e) to the low-low-pressure fluid generation step, wherein the steam condensate obtained from step e) is obtained by condensing the low-low-pressure steam, and wherein
in step f), the steam condensate obtained from step e) is transferred to the low-low-pressure fluid generation step by the weight of the steam condensate.

12. The process for urea production according to claim 1, wherein step g) is present.

13. An apparatus for urea production, comprising:
a synthesis reactor comprising a urea synthesis solution generated from ammonia and carbon dioxide;
a high-pressure decomposer configured to, by heating the urea synthesis solution generated by the synthesis reactor, decompose ammonium carbamate and separate a gaseous mixture containing ammonia and carbon dioxide from the urea synthesis solution; and
a condenser configured to absorb and condense at least a part of the gaseous mixture obtained by the high-pressure decomposer in an absorption medium and generate a low-pressure steam from a steam condensate with use of heat generated during the condensation, the apparatus for urea production further comprising:

a first heat exchange structure configured to heat-exchange a steam condensate having a temperature higher than 90° C. with another fluid to cool the steam condensate to 90° C. or less;

a second heat exchange structure configured to, by heat-exchanging the steam condensate obtained from the first heat exchange structure with a further fluid having a temperature lower than a temperature of the low-pressure steam, heat the steam condensate obtained from the first heat exchange structure; and one or more lines for providing the steam condensate obtained from the second heat exchange structure to the condenser as the steam condensate for generating the low-pressure steam.

14. The apparatus for urea production according to claim 13, comprising:

a purification apparatus configured to, by heating, at a pressure lower than the pressure in the high-pressure decomposer and higher than atmospheric pressure, the urea synthesis solution after being processed by the high-pressure decomposer to generate a gas phase and a liquid phase, and by separating the gas phase, obtain a urea synthesis solution having an increased urea concentration and generate a low-pressure steam condensate, a part of the low-pressure steam generated by the condenser being used as a heat source for heating the urea synthesis solution after being processed by the high-pressure decomposer;

a concentration apparatus configured to, by heating, at a pressure lower than the pressure in the purification apparatus and equal to or lower than the atmospheric pressure, the urea synthesis solution after being processed by the purification apparatus to generate a gas phase and a liquid phase, and by separating the gas phase, obtain a urea synthesis solution having a further increased urea concentration and generate a low-pressure steam condensate, another part of the low-pressure steam generated by the condenser being used as a heat source for heating the urea synthesis solution after being processed by the purification apparatus; and a low-low-pressure fluid generating apparatus configured to, by reducing in pressure at least a part of the low-pressure steam condensate obtained from one or both of the purification apparatus and the concentration apparatus to a pressure equal to or higher than the atmospheric pressure, generate a low-low-pressure steam condensate and a low-low-pressure steam, wherein the first heat exchange structure is configured to use the low-low-pressure steam condensate as the steam condensate having a temperature higher than 90° C.

15. The apparatus for urea production according to claim 14, wherein the pressure equal to or higher than the atmospheric pressure in the low-low-pressure fluid generating apparatus is 2 bar or more.

16. The apparatus for urea production according to claim 13, wherein the apparatus for urea production is configured so that an amount of the steam condensate supplied to the condenser is larger than an amount of the low-pressure steam generated in the condenser, and that a fluid containing the low-pressure steam and a steam condensate is obtained from the condenser, the apparatus for urea production comprises a gas-liquid separator configured to separate the fluid containing the low-pressure steam and the steam condensate obtained from the condenser into the low-pressure steam and the steam condensate, and the first heat exchange structure is configured to use the steam condensate separated by the gas-liquid separator as the steam condensate having a temperature higher than 90° C.

17. The apparatus for urea production according to claim 13, wherein the high-pressure decomposer is configured to heat the urea synthesis solution generated by the synthesis reactor with use of a medium-pressure steam as a heat source and obtain a medium-pressure steam condensate, and the first heat exchange structure is configured to use, as the steam condensate having a temperature higher than 90° C.:

the medium-pressure steam condensate obtained from the high-pressure decomposer, or a medium-pressure steam condensate obtained by cooling, through heat exchange, the medium-pressure steam condensate obtained from the high-pressure decomposer, or a medium-low-pressure steam condensate obtained from a medium-low-pressure steam generating apparatus configured to, by reducing in pressure the medium-pressure steam condensate obtained from the high-pressure decomposer to a medium-low pressure, generate a medium-low-pressure steam and a medium-low-pressure steam condensate, or a medium-low-pressure steam condensate obtained by cooling, through heat exchange, the medium-low-pressure steam condensate obtained from the medium-low-pressure steam generating apparatus.

18. The apparatus for urea production according to claim 13, wherein the first heat exchange structure is configured to use, as said another fluid, raw material ammonia to be supplied to at least one selected from the synthesis reactor, the high-pressure decomposer and the condenser.

19. The apparatus for urea production according to claim 13, comprising:

a purification apparatus configured to, by heating, at a pressure lower than the pressure in the high-pressure decomposer and higher than atmospheric pressure, the urea synthesis solution after being processed by the high-pressure decomposer to generate a gas phase and a liquid phase, and by separating the gas phase, obtain a urea synthesis solution having an increased urea concentration and generate a low-pressure steam condensate, a part of the low-pressure steam generated by the condenser being used as a heat source for heating the urea synthesis solution after being processed by the high-pressure decomposer;

a concentration apparatus configured to, by heating, at a pressure lower than the pressure in the purification apparatus and equal to or lower than the atmospheric pressure, the urea synthesis solution after being processed by the purification apparatus to generate a gas phase and a liquid phase, and by separating the gas phase, obtain a urea synthesis solution having a further increased urea concentration and generate a low-pressure steam condensate, another part of the low-pressure steam generated by the condenser being used as a heat source for heating the urea synthesis solution after being processed by the purification apparatus; and a granulating apparatus configured to produce granular solid urea, with use of air, from the urea synthesis solution after being processed by the concentration apparatus, wherein the first heat exchange structure is configured to use, as said another fluid, the air to be supplied to the granulating apparatus.

20. The apparatus for urea production according to claim 13, comprising a recovering apparatus configured to absorb and condense, in an absorption medium, at least one gas of the following gas I and gas II;

gas I is a gas remaining uncondensed in the condenser, and gas II is a gas obtained as a gas phase separated by a purification apparatus when the apparatus for urea production comprises the purification apparatus, and simultaneously cool the absorption medium, which has absorbed the at least one gas, to obtain a recovered liquid containing ammonia and carbon dioxide, wherein the purification apparatus is an apparatus configured to, by heating, at a pressure lower than the pressure in the high-pressure decomposer and higher than atmospheric pressure, the urea synthesis solution after being processed by the high-pressure decomposer to generate a gas phase and a liquid phase, and by separating the gas phase, obtain a urea synthesis solution having an increased urea concentration and generate a low-pressure steam condensate, a part of the low-pressure steam generated by the condenser being used as a heat source for heating the urea synthesis solution after being processed by the high-pressure decomposer, and the second heat exchange structure is configured to, by heat-exchanging the absorption medium, which has absorbed the at least one gas, with the steam condensate obtained from the first heat exchange structure, perform the cooling in the recovering apparatus together with the heating in the second heat exchange structure.

21. The apparatus for urea production according to claim 13, comprising a recovering apparatus configured to absorb and condense, in an absorption medium, at least one gas of the following gas I and gas II:

gas I is a gas remaining uncondensed in the condenser, and gas II is a gas obtained as a gas phase separated by a purification apparatus when the apparatus for urea production comprises the purification apparatus, and simultaneously cool the absorption medium, which has absorbed the at least one gas, to obtain a recovered liquid containing ammonia and carbon dioxide, wherein the purification apparatus is an apparatus configured to, by heating, at a pressure lower than the pressure in the high-pressure decomposer and higher than atmospheric pressure, the urea synthesis solution after being processed by the high-pressure decomposer to generate a gas phase and a liquid phase, and by separating the gas phase, obtain a urea synthesis solution having an increased urea concentration and generate a low-pressure steam condensate, a part of the low-pressure steam generated by the condenser being used as a heat source for heating the urea synthesis solution after being processed by the high-pressure decomposer, the recovering apparatus is configured to perform the cooling in the recovering apparatus by heat exchange with hot water, and the second heat exchange structure is configured to perform the heating in the second heat exchange structure by heat-exchanging the hot water after being used for the cooling in the recovering apparatus with the steam condensate obtained from the first heat exchange structure.

22. The apparatus for urea production according to claim 13, comprising:

a purification apparatus configured to, by heating, at a pressure lower than the pressure in the high-pressure decomposer and higher than atmospheric pressure, the urea synthesis solution after being processed by the high-pressure decomposer to generate a gas phase and a liquid phase, and by separating the gas phase, obtain a urea synthesis solution having an increased urea concentration and generate a low-pressure steam condensate, a part of the low-pressure steam generated by the condenser being used as a heat source for heating the urea synthesis solution after being processed by the high-pressure decomposer;

a concentration apparatus configured to, by heating, at a pressure lower than the pressure in the purification apparatus and equal to or lower than the atmospheric pressure, the urea synthesis solution after being processed by the purification apparatus to generate a gas phase and a liquid phase, and by separating the gas phase, obtain a urea synthesis solution having a further increased urea concentration and generate a low-pressure steam condensate, another part of the low-pressure steam generated by the condenser being used as a heat source for heating the urea synthesis solution after being processed by the purification apparatus; and a low-low-pressure fluid generating apparatus configured to, by reducing in pressure at least a part of the low-pressure steam condensate obtained from one or both of the purification apparatus and the concentration apparatus to a pressure equal to or higher than the atmospheric pressure, generate a low-low-pressure steam condensate and a low-low-pressure steam, wherein the second heat exchange structure is configured to, by heat-exchanging the low-low-pressure steam with the steam condensate obtained from the first heat exchange structure, perform the heating in the second heat exchange structure and condense the low-low-pressure steam by cooling the low-low-pressure steam to obtain a steam condensate.

23. The apparatus for urea production according to claim 22, comprising a line for returning, to the low-low-pressure fluid generating apparatus, the steam condensate obtained by condensing the low-low-pressure steam in the second heat exchange structure, wherein the apparatus for urea production is configured to transfer, through this line, the steam condensate obtained by condensing the low-low-pressure steam in the second heat exchange structure to the low-low-pressure fluid generating apparatus by the weight of the steam condensate.

24. The apparatus for urea production according to claim 13, comprising a heat exchange structure configured to heat-exchange the steam condensate heated by the second heat exchange structure with the low-pressure steam generated by the condenser to heat this steam condensate before providing this steam condensate to the condenser as the steam condensate for generating the low-pressure steam.

* * * * *